(12) United States Patent
Martin

(10) Patent No.: US 12,714,551 B2
(45) Date of Patent: Aug. 25, 2026

(54) ACCESSORY DEVICE TO PROVIDE NEUROPROTECTION DURING INTERVENTIONAL PROCEDURES

(71) Applicant: Maduro Discovery, LLC, Campbell, CA (US)

(72) Inventor: Brian B. Martin, Santa Cruz, CA (US)

(73) Assignee: Maduro Discovery, LLC, Los Gatos, CA (US)

( * ) Notice: Subject to any disclaimer, the term of this patent is extended or adjusted under 35 U.S.C. 154(b) by 403 days.

(21) Appl. No.: 18/351,977

(22) Filed: Jul. 13, 2023

(65) Prior Publication Data

US 2024/0016596 A1 Jan. 18, 2024

Related U.S. Application Data

(60) Provisional application No. 63/368,624, filed on Jul. 15, 2022.

(51) Int. Cl.
*A61F 2/90* (2013.01)
*A61F 2/01* (2006.01)

(52) U.S. Cl.
CPC ................ *A61F 2/013* (2013.01); *A61F 2/90* (2013.01); *A61F 2230/0067* (2013.01)

(58) Field of Classification Search
CPC .. A61F 2/01; A61F 2/011; A61F 2/013; A61F 2/90; A61F 2002/018; A61F 2230/001; A61F 2230/0067; A61F 2250/0039
See application file for complete search history.

(56) References Cited

U.S. PATENT DOCUMENTS

| | | | |
|---|---|---|---|
| 6,306,163 | B1 | 10/2001 | Fitz |
| 6,361,545 | B1 | 3/2002 | Macoviak et al. |
| 8,206,412 | B2 | 6/2012 | Galdonik et al. |
| 10,188,498 | B2 | 1/2019 | Kashkarov et al. |
| 11,020,211 | B2 | 6/2021 | Martin |
| 11,684,465 | B2 | 6/2023 | Martin |
| 2002/0183783 | A1 | 12/2002 | Shadduck |
| 2006/0142796 | A1 | 6/2006 | Weber et al. |
| 2007/0060945 | A1 | 3/2007 | Gilson et al. |
| 2007/0167974 | A1 | 7/2007 | Cully et al. |
| 2008/0167708 | A1 | 7/2008 | Molland et al. |
| 2009/0069841 | A1 | 3/2009 | Pah |
| 2009/0326575 | A1 | 12/2009 | Galdonik et al. |

(Continued)

FOREIGN PATENT DOCUMENTS

| | | |
|---|---|---|
| JP | 2011-525405 | 9/2011 |
| JP | 2012-500049 | 1/2012 |

(Continued)

*Primary Examiner* — Tan-Uyen T Ho
*Assistant Examiner* — Lindsey R. Rivers
(74) *Attorney, Agent, or Firm* — Levine Bagade Han LLP

(57) ABSTRACT

Devices, systems and methods for filtering embolic particles that may be generated from a medical procedure including protection of the major branching vessels from the aorta, and catches and filters emboli that may be generated during the TAVR procedure. The filter devices disclosed herein form an improved seal against the vessel wall that is activated by flowing blood. Devices described herein also allow for the closing of the ends of the filter device after capture of emboli, providing further security against accidental loss of emboli post capture.

20 Claims, 30 Drawing Sheets

(56) References Cited

U.S. PATENT DOCUMENTS

| | | | |
|---|---|---|---|
| 2011/0137399 | A1 | 6/2011 | Chomas et al. |
| 2012/0172916 | A1 | 7/2012 | Fifer et al. |
| 2013/0289716 | A1 | 10/2013 | Don Michael |
| 2014/0249568 | A1 | 9/2014 | Adams et al. |
| 2014/0277096 | A1 | 9/2014 | Richter et al. |
| 2014/0288588 | A1 | 9/2014 | Lam et al. |
| 2015/0209136 | A1 | 7/2015 | Braido et al. |
| 2016/0120636 | A1 | 5/2016 | Gera et al. |
| 2017/0014229 | A1 | 1/2017 | Nguyen-Thien-Nhon et al. |
| 2017/0181835 | A1 | 6/2017 | Kleshinski et al. |
| 2017/0231749 | A1 | 8/2017 | Perkins et al. |
| 2019/0336264 | A1 | 11/2019 | Behfar et al. |
| 2020/0054432 | A1 | 2/2020 | Martin |
| 2021/0022845 | A1 | 1/2021 | Martin |
| 2023/0277290 | A1 | 9/2023 | Martin |
| 2025/0241739 | A1 | 7/2025 | Martin |

FOREIGN PATENT DOCUMENTS

| | | | | |
|---|---|---|---|---|
| JP | 7237997 | | 3/2023 | |
| WO | WO-0238085 | A1 * | 5/2002 | ............... A61F 2/90 |
| WO | WO 2013/033791 | | 3/2013 | |
| WO | WO-2013154765 | A2 * | 10/2013 | ............. A61F 2/013 |
| WO | WO 2017/024258 | | 2/2017 | |
| WO | WO 2019/191281 | | 10/2019 | |
| WO | WO 2024/015921 | | 1/2024 | |

* cited by examiner 102
100
102

102
100
12
102

102
100
12
102

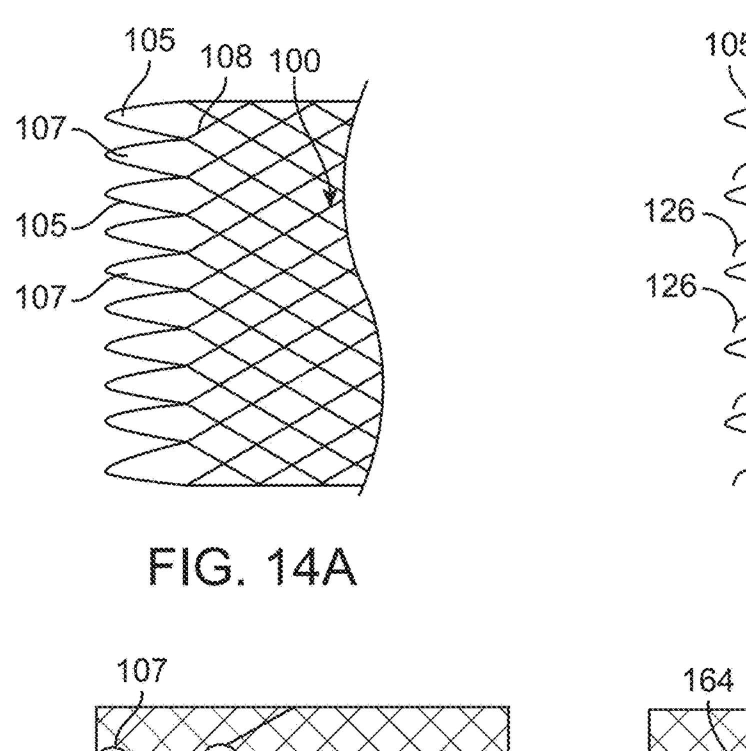
FIG. 14A
FIG. 14B
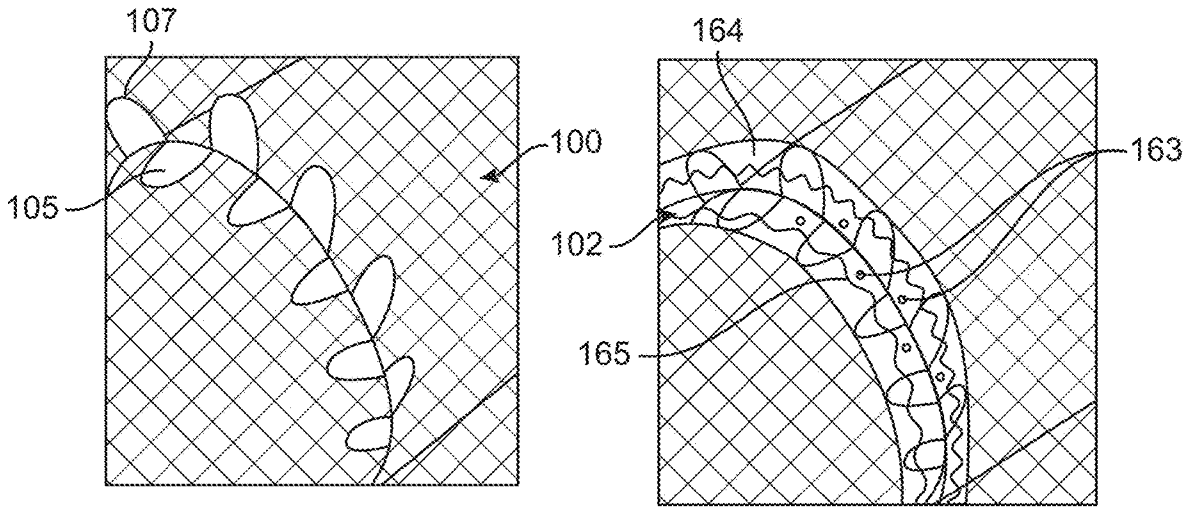
FIG. 14C
FIG. 14D
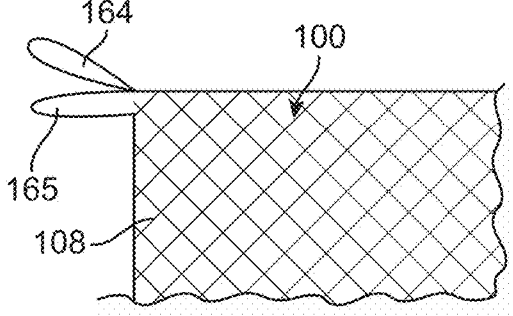
FIG. 14E

ACCESSORY DEVICE TO PROVIDE NEUROPROTECTION DURING INTERVENTIONAL PROCEDURES

CROSS-REFERENCE TO RELATED APPLICATIONS

This application is a non-provisional of U.S. provisional application No. 63/368,624 filed Jul. 15, 2022, the entirety of which is incorporated by reference herein.

FIELD OF THE INVENTION

Devices, systems, and methods are disclosed for filtering embolic particles that may be generated from a medical procedure, including protection of the major branching vessels from the aorta and catching and filters emboli generated during the TAVR procedure. The filter devices disclosed herein form an improved seal against the vessel wall that is activated by flowing blood. Devices described herein also allow for the closing of the ends of the filter device after capture of emboli, providing further security against accidental loss of emboli post-capture. The TAVR procedure is just one application where the use of the devices, systems, and methods provides improved benefits. However, the devices, systems, and methods can be used in any portion of the body.

BACKGROUND OF THE INVENTION

Percutaneous coronary valve interventions, including both valve replacements and valve repairs, are a rapidly growing segment of catheter-based medical interventions. Catheter-based interventions have recently been a growing sector in cardiac interventions and currently include mitral valve repairs and aortic valve repairs and replacements. One segment of this growing market is aortic valve replacements, referred to as Transcatheter Aortic Valve Replacement ("TAVR"). While TAVR procedures are increasing in frequency and with much success, the procedure has a risk of dislodging a clot or thrombi within the vasculature in the form of thrombus and/or pieces of stenosis. These clots can potentially cause ischemic cerebral stroke if they travel to the brain, lungs, or to the peripheral vessels.

Efforts have been taken to reduce the risk of stroke through the development of medical devices designed to prevent the dislodged clot from traveling to the brain. While these devices have met some success, there remains a significant need for further refinement and improvement.

The previous devices generally fall into two classifications: deflector devices and capture devices. Deflectors act to "deflect" thrombus away from critical vessels that lead to the brain and usually entail deploying a nitinol mesh material (or similar) to prevent passage of the thrombus/stenosis fragment into critical vessels leading to the brain. A physician will temporarily deploy the mesh material over the origin of the vessels leading to the brain so that blood can continue flowing, but clot-causing materials cannot get through the mesh pores (usually around 100 microns pore size). Since the clot material is not captured, it travels elsewhere in the body, usually down the ascending aorta and into the peripheral vasculature. For example, FIG. 1A illustrates an aortic arch 2, left subclavian artery 4, left common carotid artery 6, and brachiocephalic trunk (innominate artery) 8. The left common carotid artery 6 and the brachiocephalic trunk 8 supply blood to the head and neck. Therefore, any migration of emboli 30 poses a risk if the emboli 30 travel through these arteries and into the brain.

FIGS. 1A to 1C show examples of conventional vascular protection devices. For example, FIG. 1A shows a capture device called the Sentinel™ by Claret Medical. As illustrated, the capture device is positioned within the left common carotid artery 6 and the brachiocephalic trunk 8 to prevent emboli 30 from migrating. However, it has been published in the medical literature that these filters do not adequately fit within the anatomy in at least 10% of the cases, which creates a risk of emboli passing. FIGS. 1B and 1C show examples of deflector devices 24, 26. As shown, the deflector devices 24, 26 prevent emboli from entering the branching vessels. Moreover, if any of the conventional devices do not form an adequate seal against the vessel wall, thrombi can pass by the device (i.e., between the device and the vessel wall) and flow to the brain, causing cerebral ischemic strokes.

There are additional limitations with deflector devices. First, in most devices, clot material is not captured or removed from the body. While it is advantageous to prevent the clot material from traveling to the brain and causing an ischemic stroke, the device deflects clots to the peripheral vessels. While less dangerous, the clots can still lead to blockages in the legs, renal vessels, etc. Additionally, the deflector devices also do not form an effective seal in the vasculature, meaning that while some or even most of the clot might be prevented from entering the vessels leading to the brain, a clot can still pass by the device, creating a risk of a stroke.

Apart from the above, conventional capture devices have more additional limitations. Some of the capture devices do not protect all of the vessels leading to the brain (there are three main vessels that branch from the aorta and lead to the brain: the brachiocephalic artery, which then feeds the right subclavian and right common carotid arteries, the left common carotid artery, and the left subclavian artery). The Sentinel device, made by Claret Medical (Santa Rosa, CA), protects only 2 of the 3 branching vessels. Other capture devices, such as the Emboliner device, made by Emboline (Santa Cruz, CA), use a nitinol mesh cylinder to attempt to provide coverage across all three branching vessels but may fail if the seal between the mesh cylinder and the aortic wall is suboptimal, and allow a clot to pass between the mesh cylinder and vessel, allowing a clot to flow to the brain and cause a stroke.

In fact, sub-adequate contact between the deflector/capture device and the vessel wall is a problem for all of the current cerebral protection devices. The imperfect seal allows for the passage of small clots to the brain, creating a risk of stroke. Current medical literature states that these filters do not adequately "fit" the anatomy in at least 10% of cases.

Another limitation of the current capture devices is the risk that once captured, the clot can potentially dislodge and travel back into the bloodstream. Both the Sentinel device and the Emboliner device capture clots, but the distal end of the device remains open. Upon removal of the device from the body at the end of the procedure, clots can migrate from the distal end. This could occur if the device collapses or geometrically distorts during removal, if the device scrapes against plaque and distorts during removal, or if the blood flow pulsations (so close to the heart) create flow distortions that dislodge the clot from the filter.

There remains a need for improved devices and methods to address the problems discussed above. While the discussion focuses on applications for protecting the cerebral vasculature, the improved devices and methods described below have applications for protecting any part of the vasculature.

BRIEF SUMMARY OF THE INVENTION

The examples discussed herein show variations of protection devices, systems, and methods that are suitable to protect vasculature or other fluid-filled passages from debris caused during procedures that are performed upstream to the site at which the protection device is delivered, or the protective system and/or method is applied. The term emboli can include particles generated by a blood clot, plaque, cholesterol, thrombus, calcifications, naturally occurring foreign bodies (i.e., a part of the body that is lodged within the lumen), a non-naturally occurring foreign body (i.e., a portion of a medical device or other non-naturally occurring substance lodged within the lumen.) However, the devices are not limited to such applications and can apply to any number of medical applications where protection of the vascular or passage is required.

Variations of the inventions described herein include protection systems for reducing migration of emboli within a blood flow of a vessel. Additional variations of the invention include methods and devices for forming an improved seal against a wall of a vessel using a blood flow within the vessel. For example, one such medical device can include a device body configured to navigate through the vessel; a tubular member circumferentially positioned about the device body, the tubular member having a far portion that is expandable away from the device body and a near portion coupled to the device body; a filter body positioned exterior to the device body and coupled to the tubular member, where the filter body comprises a distal portion, a proximal portion, and a fluid permeable wall extending therebetween, where the distal portion is coupled to extending therebetween, where the distal portion is coupled to the far portion and the proximal portion is coupled to the device body such that when the device body is positioned in the vessel the far portion and distal portion expand allowing the blood flow to enter the filter body and pass through the fluid permeable wall while retaining emboli in the filter body; an outer sail member located circumferentially about an exterior of the far portion of the tubular member, where the blood flow into the tubular member enters an interior of the outer sail member causing the outer sail member to move radially outward from the tubular member such that an exterior of the outer sail member forms a conformable seal against a wall of the vessel; and a diverting surface positioned interior to the tubular member and radially adjacent to the outer sail member, the diverting surface configured to provide resistance to the blood flow, where a second end of the diverting surface is joined to the tubular member and a first end of the diverting surface extends inwardly from the tubular member away from the outer sail member to direct the blood flow towards the outer sail member.

Another variation of a medical device that forms an improved seal against a vessel wall of a vessel using a fluid flow within the vessel includes a tubular member having a far portion, a near portion, and a wall extending therebetween; an outer sail member located circumferentially about an exterior of the far portion of the tubular member, where the fluid flow into the tubular member enters an interior of the outer sail member causing the outer sail member to move radially outward from the tubular member such that an exterior of the outer sail member forms a conformable seal against the vessel wall; and a diverting surface located interior to the tubular member and radially adjacent to the outer sail member, the diverting surface having a first end, a second end, and an intermediate portion extending therebetween, where the first end extends inwardly away from the outer sail member causing the intermediate portion to direct the fluid flow towards the outer sail member.

The present disclosure includes methods for filtering a body passage for emboli dislodged during a procedure performed within the body passage of a patient, the method comprising: positioning a filter device at a deployment site in the body passage, where the deployment site is downstream of a procedure site; deploying the filter device such that a blood flow towards the filter device causes an external sail located about an outer perimeter of the filter device to move away from the filter device and form a seal against a wall of the body passage, where a diverting surface located with of the body passage, where a diverting surface located within the filter device redirects a portion of the blood flow towards an interior of the external sail, and where a body of the filter device permits passage of the blood flow while restricting flow of emboli such that emboli within the blood flow are retained within the filter device; securing the filter device and emboli located therein after the procedure; and removing the filter device and emboli from the body passage.

In another variation, a system can include a filter body having a distal portion and a proximal portion, where the filter body is configured for positioning within the vessel such that the blood flow enters the distal portion, wherein a wall of the filter body is porous to permit passage of the blood flow therethrough while capturing emboli within the blood flow; a sealing membrane located circumferentially on the distal portion, where the sealing membrane deflects from the filter body as a result of blood flow against the sealing membrane, wherein the deflection of the sealing membrane permits creation of a seal against a wall of the vessel; and a catheter body configured to navigate through the vessel, where the filter body is configured about an exterior of the catheter body.

In another variation, the inventions described herein include protection systems for reducing migration of emboli within a blood flow of a vessel. For example, such a system can include a filter body having a distal portion and a proximal portion, where the filter body is configured for positioning within the vessel such that the blood flow enters the distal portion, wherein a wall of the filter body is porous to permit passage of the blood flow therethrough while capturing emboli within the blood flow; a sealing membrane located circumferentially on the distal portion, where the sealing membrane deflects from the filter body as a result of blood flow against the sealing membrane, wherein the deflection of the sealing member permits creation of a seal against a wall of the vessel; and a catheter body configured to navigate through the vessel, where the filter body is configured to re-enter the catheter body such that the filter body and emboli located therein are protected within the catheter body upon removal from the patient.

The sealing membranes can optionally comprise a fluid-impermeable material. In some variations, the sealing membrane can have one or more openings to control the building of pressure at the sealing membrane. A variation of the sealing member can comprise an expandable portion such that blood flow against the sealing membrane causes expansion of the expandable portion. In additional variations, the sealing membrane comprises a thin film polymer or elastomer.

The sealing membranes can be located within the filter body. Alternatively, or in combination, the sealing membranes can be located on an exterior portion of the filter body. In yet another variation, the sealing membrane is located on an interior diameter of the filter body, and a second sealing membrane is located on an exterior of the filter body, wherein blood flow causes deflection of the sealing membrane to increase an effective sealing area of the filter device. In an additional variation, the sealing membrane comprises a first layer and a second layer, where the first layer is adjacent to an outer surface of the filter device, and the second layer is adjacent to an interior passage of the filter device. In one variation, the first layer is connected to the second layer such that blood flow into a region of the sealing membrane bounded by the first layer, and the second layer increases in pressure to further enhance opening of the sealing membrane. Additionally, or in combination, the first layer is configured to expand more than the second layer such that the sealing membrane expands outward from the filter device.

Variations of the filter device include a series of petals on a distal end of the filter body, where the sealing membrane is coupled to the series of petals. The series of petals can include at least one deflected petal, and where the sealing membrane comprises a first layer coupled to the at least one deflected petal and a second layer coupled to the series of petals such that blood flow into a region between the first layer and second layer increases pressure in the region.

The filter body can comprise a mesh braid or multiple layers of mesh braids. The mesh braids can comprise super-elastic Nitinol. Alternatively or in combination, the filter body comprises a thin film polymer or elastomer.

The filter body can comprise a pore size of 40 microns to 200 microns.

In additional variations, the sealing member further expands in response to blood flow.

Variations of the devices described herein can include a proximal sealing membrane within the filter body located adjacent to the proximal portion of the device. Alternatively or in combination, the filter body comprises a sheet of material with controlled porosity. In additional variations, the filter body is composed of strips of material that overlay to form a continuous surface.

The devices described herein can include at least one pull wire coupled to the distal end such that the application of a tensile force on the pull wire urges the distal end to a closed position. In additional variations, the device can further comprise at least one resilient ring located at a distal end of the filter body to bias the distal end in an open position in the absence of the tensile force.

Any of the systems and/or devices described herein can include a synching member configured to synch a portion of the filter body.

The present invention also includes methods for filtering a vessel for emboli dislodged during a procedure performed within the vessel of a patient. For example, such a method can include positioning a filter device at a deployment site in the vessel, where the deployment site is downstream of the procedure site, a distal portion of the filter device includes a sealing member; deploying the filter device such that a blood flow towards the filter device causes the sealing member to form a seal against a wall of the vessel and where a body of the filter device permits passage of the blood flow while restricting the flow of emboli such that emboli within the blood flow are retained within the filter device; securing the filter device and emboli located therein within a catheter body after the procedure; and removing the catheter body, filter device, and emboli from the vessel.

The methods described herein can include advancing a second catheter through a proximal opening of the filter device and constricting a proximal portion of the filter device about the second catheter to prevent emboli from passing between the second catheter and the proximal opening.

In additional variations, the methods can further comprise completing the procedure and withdrawing the second catheter from the filter device while constricting the proximal portion of the filter device about the second catheter, and upon removal of the second catheter from the filter device, further constricting the filter device to prevent the escape of emboli from the proximal opening.

In one variation of the methods, securing the filter device and emboli located therein comprises withdrawing the filter device within the catheter body.

The methods can also further include restricting a distal opening of the filter device prior to withdrawing the filter device within the catheter body.

In an additional variation of the methods, the filter device comprises a proximal sealing member, wherein the blood flow causes the proximal sealing member to form a proximal seal against the second catheter. In an additional variation of the method, the filter device extends from a distal end of the catheter body.

The methods can also comprise, prior to deploying the filter device, inverting the filter device within the catheter body, and wherein deploying the filter device comprises securing a proximal end of the filter device within the catheter body while withdrawing the catheter body relative to the filter device such that the filter device everts into position within the vessel.

In another variation of the methods, prior to deploying the filter device, the filter device is inverted within the catheter body, wherein deploying the filter device comprises advancing a proximal end of the filter device out of the catheter body such that the filter device everts into position within the vessel.

A variation of the methods can also include advancing a second catheter through the catheter body and filter device to perform the procedure. In an additional variation, the method can further comprise restricting a distal end of the filter device to prevent emboli from passing through the distal end. In another variation, the method can further comprise withdrawing the distal end of the filter device into the catheter body such that the filter device inverts within the catheter body.

In an additional variation of the method, after deploying the filter device, a balloon catheter or bristle-brush device is used to loosen emboli from a procedure site in order to ensure capturing of emboli within the filter device.

The methods include positioning the filter device in an aorta. The methods can include advancing the filter device and catheter body through a radial vessel or advancing the filter device and catheter body through a femoral vessel.

In another variation, the methods can further include passing a portion of the blood flow exterior to the body of the patient through an external filter and returning the blood flow back to an artery in the patient.

Another variation of the methods described herein includes advancing a filter device to a deployment site in the vessel, where a distal portion of the filter device includes a sealing member; deploying the filter device in proximity to the procedure site, where the filter device permits the passage of blood therethrough; forming a first seal between a wall of the vessel at the deployment site using the sealing member, causing a flow of blood into the filter device; advancing a medical device through the filter device to the procedure site; performing a procedure in the vessel distally to the filter device using the medical device, where the procedure causes emboli in the flow of blood; withdrawing the medical device from the deployment site and further restricting the proximal portion of the filter device such that emboli remain within the filter device; positioning the filter device and emboli located therein within a catheter to prevent passing of emboli into the blood flow; and removing the catheter, filter device, and emboli from the patient.

Variations of the methods described herein can further include constricting a proximal portion of the filter device about the medical device to form a second seal about the medical device after advancing the medical device through the filter device.

DESCRIPTION OF THE DRAWINGS

Each of the following figures diagrammatically illustrates aspects of the invention. Variations of the invention from the asp aspects shown in the figures are contemplated.

FIGS. 14A to 14E show another variation of a filter device with a multi-layer seal.

DETAILED DESCRIPTION

It is understood that the examples below discuss uses in the aortic arch to protect cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

FIGS. 2A to 2I illustrate an example of the flow-assisted sealing of the present disclosure. In this variation, a guidewire 110 advances through the left subclavian artery 4 to permit the positioning of a filter system (not shown in FIG. 2A) using a radial artery approach. Such an approach allows a TAVR system to be delivered from a femoral artery without the filter system reducing the available space within the vessel. Many TAVR systems are large, typically 12-18 French in diameter, so variations of a filter system that is also delivered from the femoral artery might compete for space within this vessel. Delivering the filter system from the radial artery allows for the space within the femoral artery to accommodate the TAVR system and other necessary devices.

The seal, filter device, and/or guide catheter can have any number of coatings to minimize thrombogenicity, minimize platelet activity, or provide other drug-eluting benefits as needed. Alternatively, or in combination, the seal, filter device, and/or guide catheter can include a hydrophilic coating.

Figure 2A:
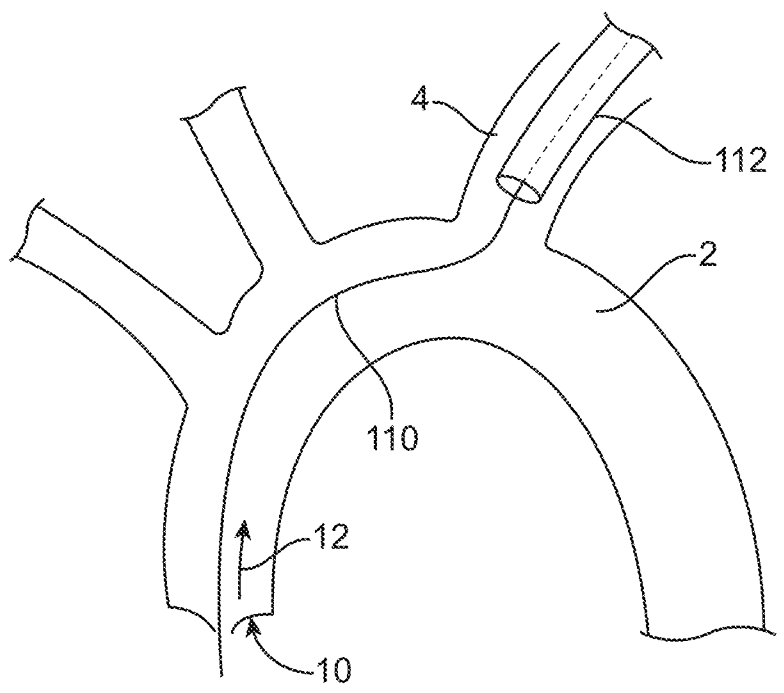
FIGS. 2A to 2I illustrate an example of the flow-assisted sealing of the present disclosure.
Figure 2B:
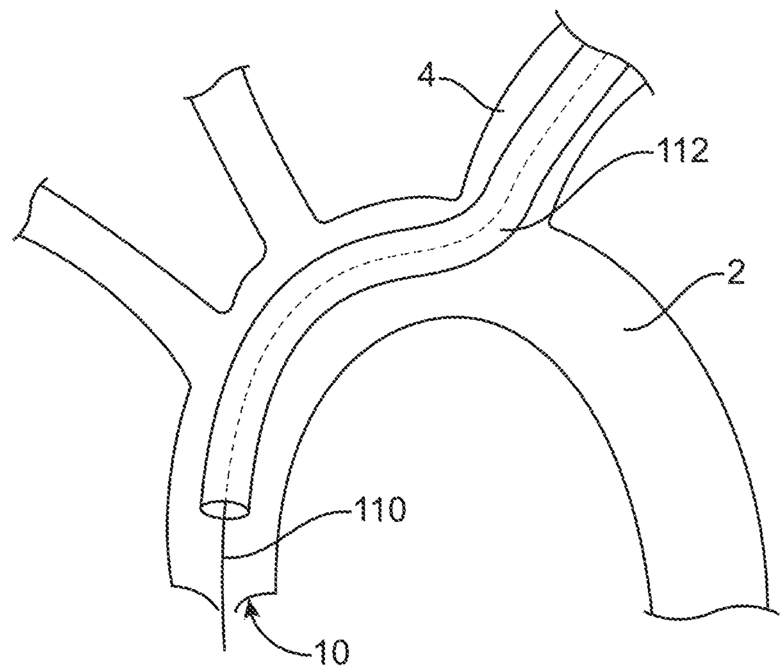

As shown in FIG. 2A, a guidewire 110 can be introduced from a radial artery through the left subclavian artery 4, into the aortic arch 2, to the aortic valve 10. A guide catheter or guide sheath 112 can be introduced over the guidewire 110 and advanced to a site for deployment of the filter device, which can be downstream of the procedure site (as shown in FIG. 2B). In this example, the procedure site is the location of the valve 10. As noted, the guide catheter 112 can be introduced over the guidewire 110 while containing the collapsed filter system (not shown yet). Alternatively, the filter system can be advanced through the guide catheter 112 when the guide catheter 112 is properly positioned. Exemplary variations of the guide catheter 112 can range from 4F to 8F in diameter. However, any size can be used as needed. Moreover, the distal region(s) of the guide catheter can be pre-shaped with bends and angles to facilitate navigation in a desired region of the anatomy. For instance, the guide catheter 112 can have a bend proximate to the distal end to accommodate entry into the aortic arch 2 and to allow advancement of the distal end towards the valve 10.

Figure 2C:
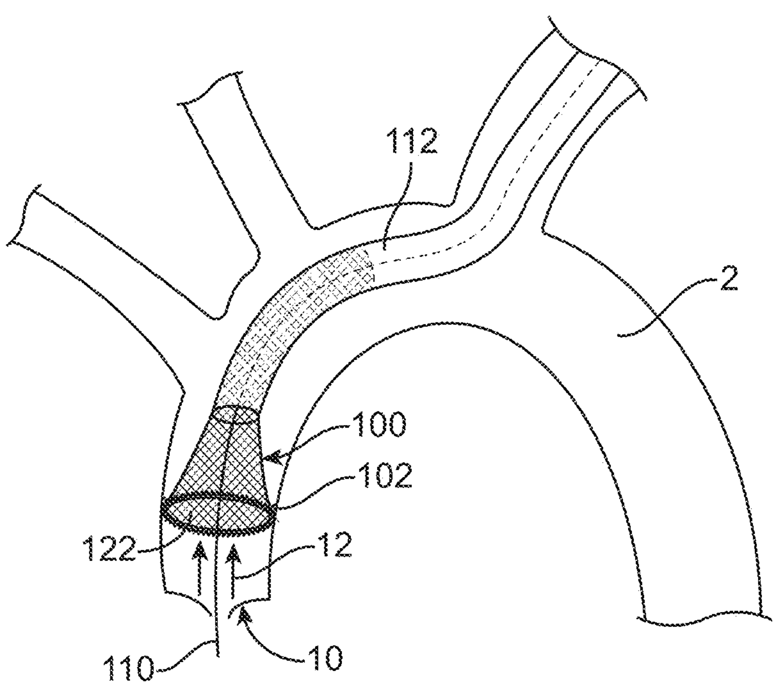

FIG. 2C illustrates the initial deployment of a filter device 100 at a deployment site in the path of blood flow 12 from the procedure site (e.g., the valve 10). The filter device 100 can be deployed by applying a force on the device 100 to urge it out of the delivery catheter 112. Alternatively, the guide catheter 112 can be pulled relative to the filter device 100 to expose the filter device 100 at the desired deployment site. Variations of the filter device 100 are constructed from a superelastic Nitinol mesh that is heat set to expand to the arterial surface (typically 2.5 cm to 3.5 cm in the aortic arch 2).

In one variation of the filter device 100, the Nitinol mesh is a single layer of woven Nitinol wires. Additional variations of the device 100 can comprise multiple mesh layers of Nitinol overlaying one another. The Nitinol wires can be round, square, or rectangular in cross-section, as well as triangular, half-round, or any combination thereof. Such irregular shapes may be preferential for limiting thrombogenic responses, as the blood patterns and flow properties may be changed due to wire shape.

Additionally, some portion of the wires could be composed of DFT (Drawn Filled Tube), where the Nitinol wire contains a core of gold, platinum, or tantalum (or similar) for radiopacity. Alternatively, individual wires of the mesh can be composed of solid or hollowed platinum, gold, and/or tantalum for radiopacity. Gold, platinum, and/or tantalum rings may also be used for radiopacity.

In one variation of the filter device 100, the Nitinol mesh has a pore size of around 100 microns, although a range of about 40 to 200 microns, or even larger, could also be appropriate.

FIG. 2C also illustrates the filter device 100 having a flow-seal 102 located at a distal end 122 of the filter device 100. This flow-seal 102 is activated by blood flow 12 into the device. Variations of the flow-seal comprise a section of impermeable soft polymer membrane that expands as blood flows into the membrane. The blood flow 12 causes the flow-seal to expand against the arterial wall to create a tight seal, which prevents the passage of emboli that are located within the blood flow 12. As noted above, conventional protective devices can fail to create a tight seal between filter device 100 and the vessel wall, which allows emboli to escape the protective device. As noted above, the wall of the aorta is usually calcified and contains plaque deposits, which creates a geometrically irregular surface that makes it difficult to form an appropriate seal using conventional devices. The flow seal shown in FIG. 2C avoids problems associated with conventional devices by using the naturally occurring blood flow 12 to expand the flow-seal 102 membrane and create a tight seal, which requires that emboli pass into the opening of the filter device 100. Additional variations of the flow-seal are discussed below.

Figure 2D:
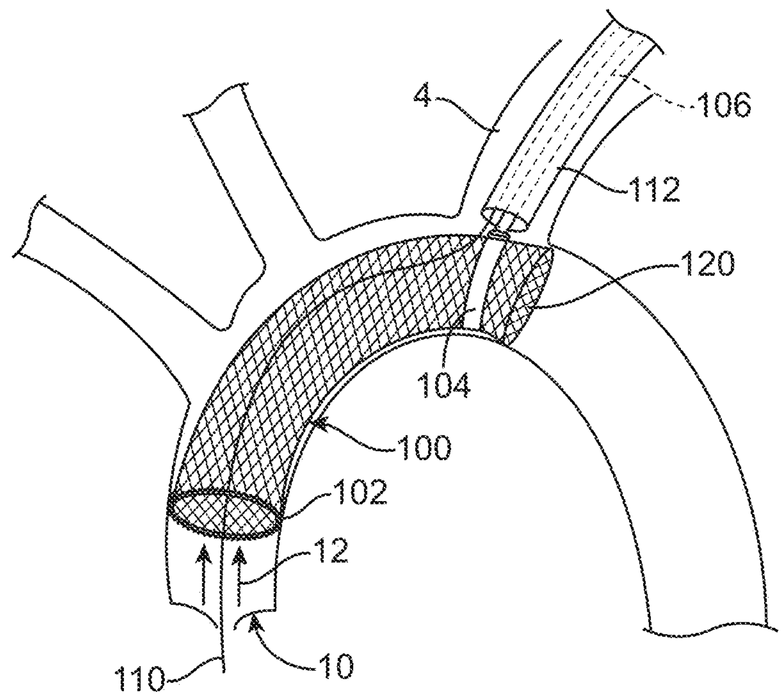

FIG. 2D illustrates a variation of a filter device 100 having an adjustable collar 104 at a proximal end of the device 100. The collar 104 can position the device as well as adjust the diameter of the proximal end 120 by application of a force on the connecting wire 106 that extends through the guide catheter 112 and through the left subclavian 4 and radial arteries. The restriction collar 104 can be used to clamp down tightly onto a catheter or device (such as a TAVR guide catheter discussed below) that is inserted into the proximal opening 120 of the device 100. Variations of the device 100 can include a polymeric liner on the ID of the mesh at or near the collar 104 location to ensure a tight seal against the catheter or device that extends therein. In one variation, the collar 104 can comprise a push-pull ribbon that controls the diameter of the filter device 100. Alternatively, as discussed below, the collar can include or is replaced with any number of ring structures that control the diameter of the filter device 100.

Figure 2E:
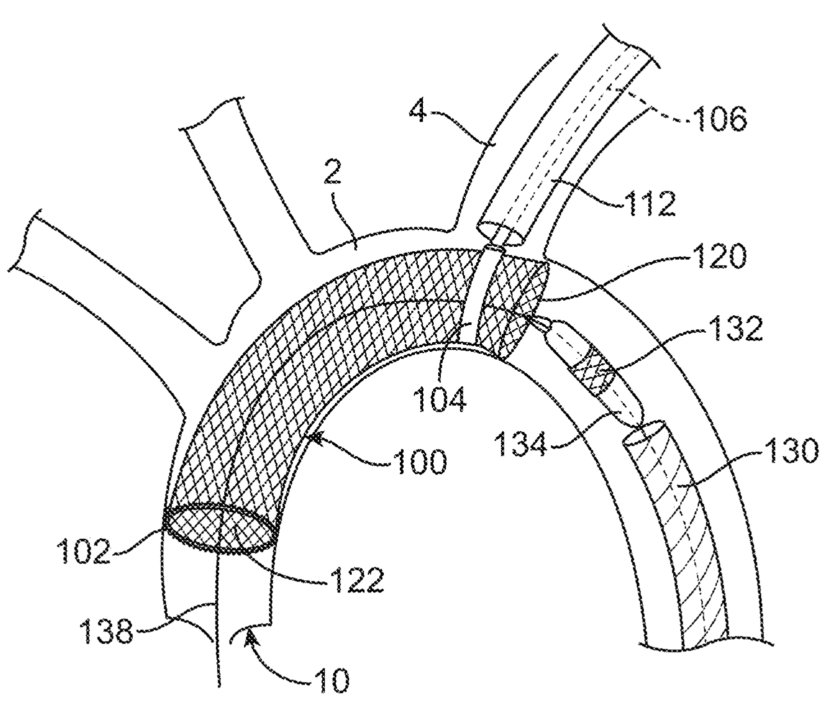

FIG. 2E shows the deployed filter device 100 in place to receive a second catheter 130 that will be used to complete a procedure within the vessel. In the illustrated example, a TAVR system is introduced through a femoral artery with the TAVR guidewire 138 advanced into the proximal opening 120 of the device 100 and through the distal opening 122 to the procedure site (again, the valve 10). Again, as discussed above, the filter device 100 maintains a circumferential seal with the flow seal 102 that remains activated by the flow of blood within the vessel. Next, as shown in FIG. 2E, a TAVR guide catheter 130, and TAVR valve 132 with balloon 134 are advanced along or over the TAVR guidewire 138. In alternate variations, additional devices (not shown), such as a pigtail catheter, infusion catheter, or pressure monitoring catheter, or guidewire, can be delivered or advanced through the filter device 100, which can accommodate multiple devices.

Figure 2F:
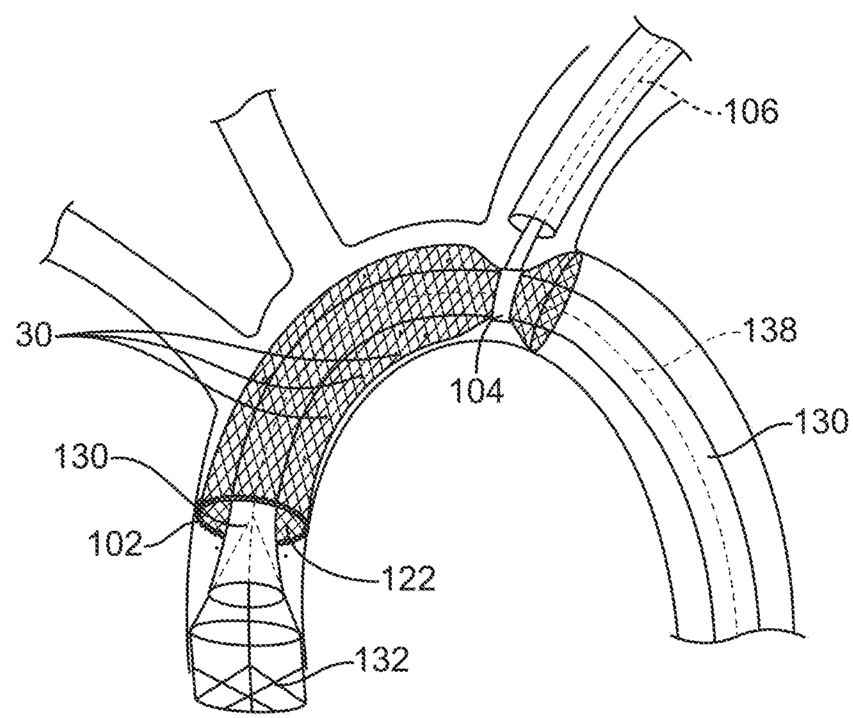

FIG. 2F illustrates a state where the TAVR guide catheter 130 passes through the filter device 100, and the TAVR valve 132 is positioned within the aortic valve 10. Once the TAVR (or other devices for the appropriate procedure) is positioned, the medical practitioner can restrict the collar 104 to form a seal against the TAVR guide catheter 130. The seal can be tight or can be sufficient to continue to allow the TAVR catheter 130 to slide therein. In some variations, a tight seal is essential for ensuring that emboli 30 trapped by the filter device 100 remain contained inside the filter mesh. As stated previously, a polymer ring or other structure on the ID of the filter at the location of the collar can be used to further enhance the seal. It should also be noted that the collar 104 can be substantially restricted as soon as the TAVR guide 130 enters the filter 100 while allowing sliding of the TAVR guide 130 relative to the collar 104 and then further restricted to form a tight seal once the TAVR guide 130 and TAVR valve 132 are in place.

FIG. 2F illustrates the situation where the TAVR valve 132 is deployed against the aortic valve, and the TAVR delivery catheter 130 is withdrawn from the procedure site. As shown, the procedure can cause embolic particles 30 to begin to migrate within the vessel. However, the flow-seal 102 will direct any embolic particle 30 flowing in the blood into the distal opening 122 of the filter device 100. Therefore, the filter device 100 traps and contains many of the embolic particles 30 that would otherwise travel to other parts of the body, such as the brain, where an embolic particle could cause an ischemic stroke.

Figure 2G:
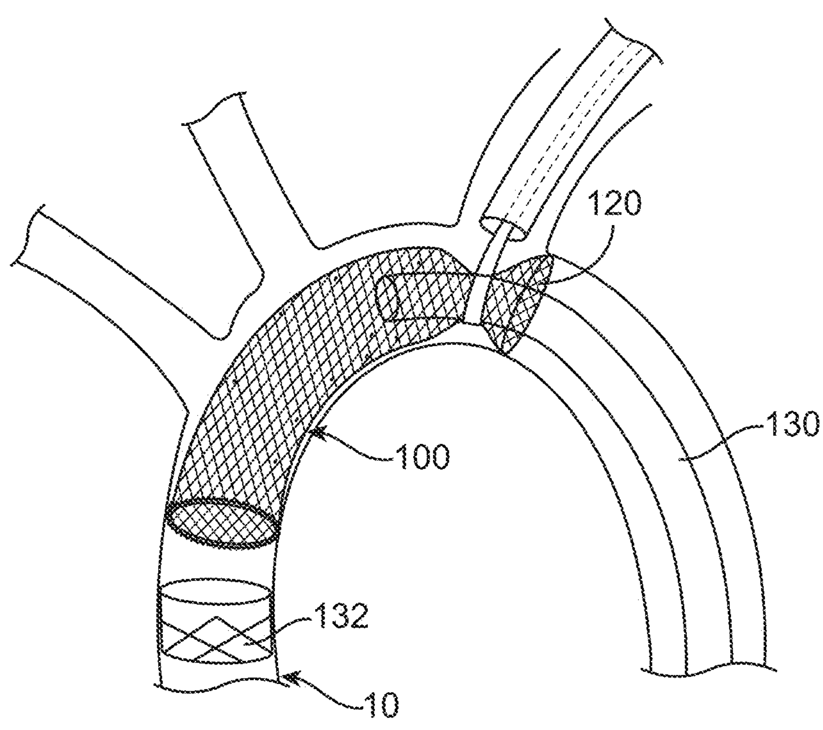
Figure 2H:
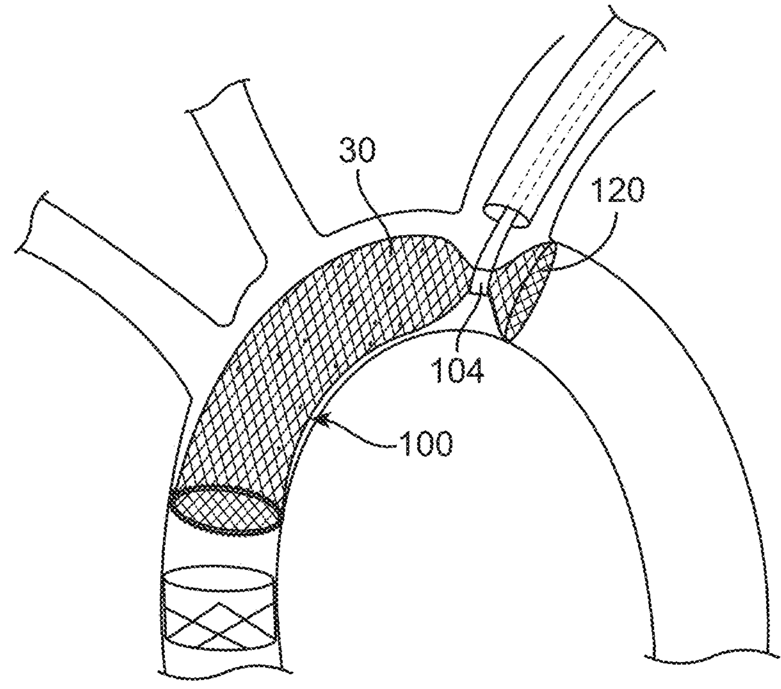

FIG. 2G shows the state after the procedure where the TAVR implant 132 is positioned at the valve 10 and where the TAVR balloon and TAVR wire are removed from the filter device 100. This leaves only the TAVR guide 130 through the filter device 100. (Note: guidewire may or may not be removed prior to TAVR guide catheter removal). FIG. 2H shows the filter device 100 after the TAVR guide is removed, but where the collar 104 further constricts the proximal portion of the filter device 100 to effectively completely close the proximal end of the filter 100. This ensures that the trapped embolic material 30 cannot escape through the proximal opening 120 of the filter device 100.

It should also be noted that a physician could elect to keep the filter device 100, as shown in FIG. 2H, in place for several hours or even days after the procedure as a precautionary means to collect any late-breaking plaque from the aortic valve. This would further provide protection against stroke.

Figure 2I:
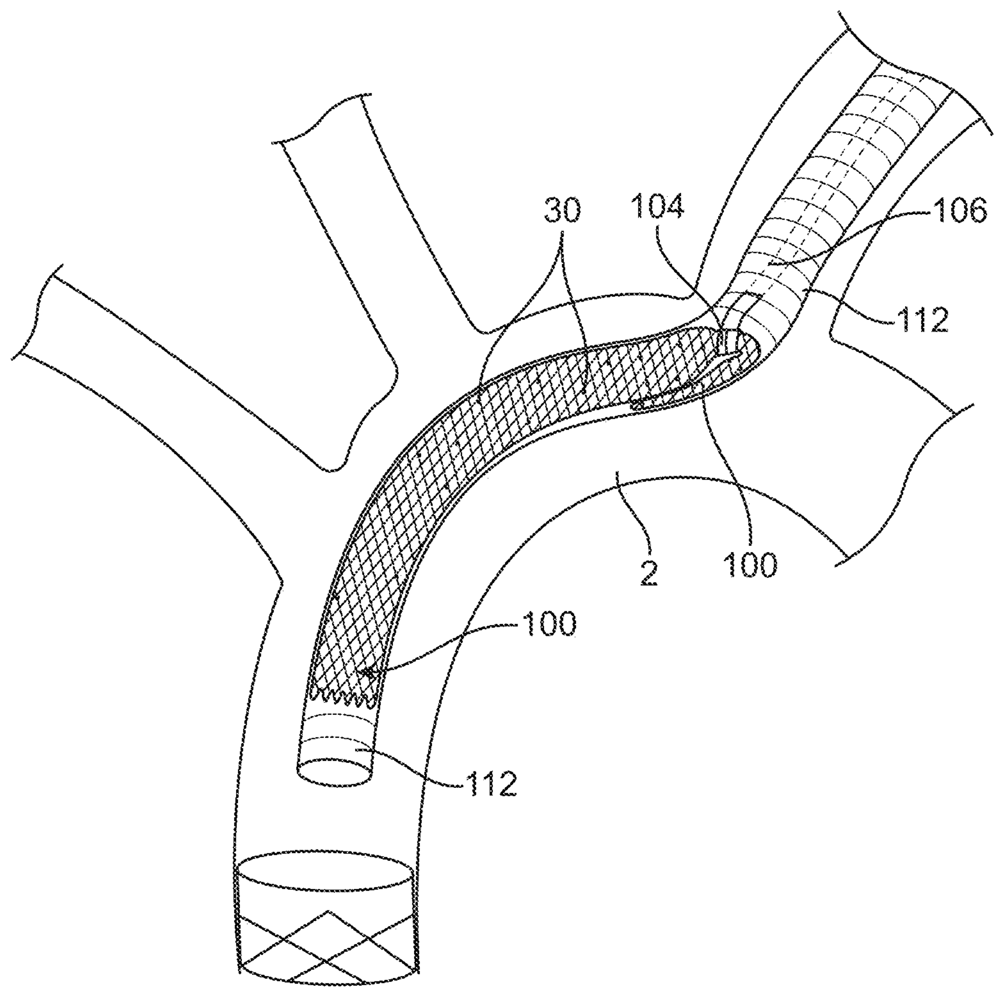

FIG. 2I illustrates a condition where the filter device 100 is ready for removal. The filter device 100 can be withdrawn into the guide catheter 112. Alternatively, the guide catheter 112 can be advanced over the filter device 100, resulting in a collapse of the filter device 100 as it is constrained inside the guide catheter 112. Since the filter device, 100 is constrained inside the inside the guide catheter 112. The embolic particles 30 are now protected from escaping. Once secured, the guide catheter 112 and filter device 100 are removed.

Figure 3:
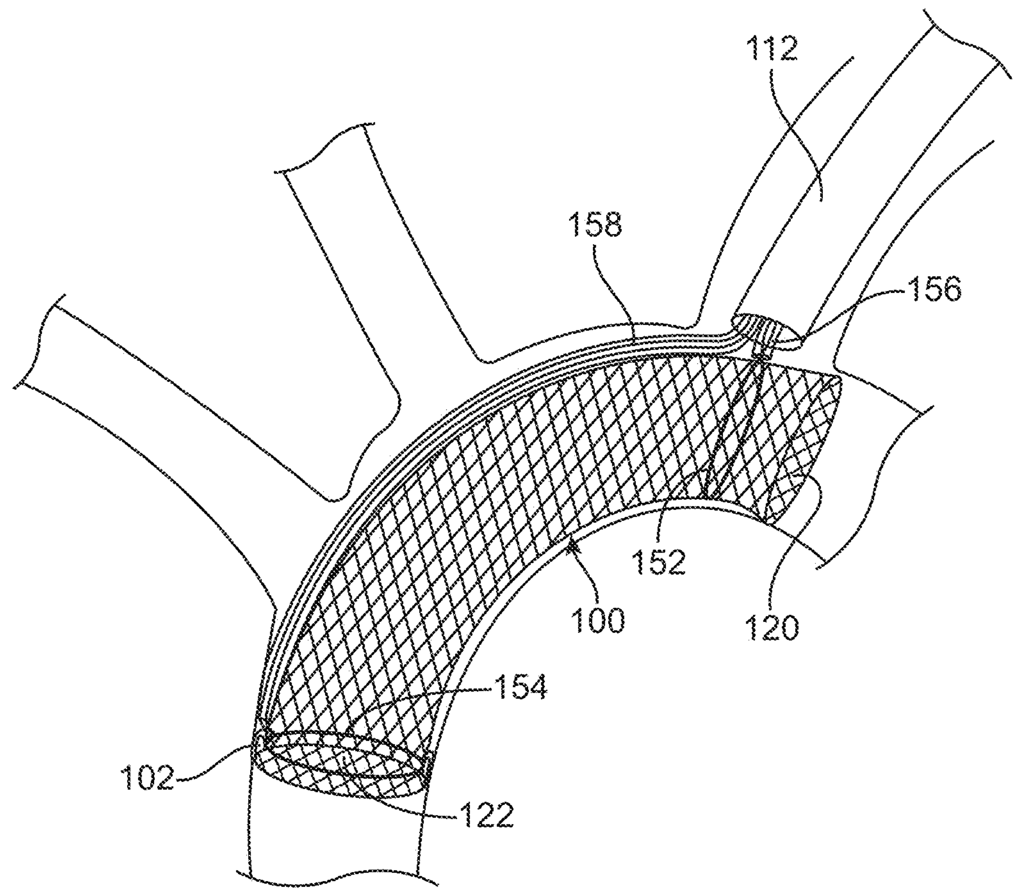
FIG. 3 shows a variation of a filter device 100 with a collar comprising a lasso-type mechanism that can adjust a diameter of a portion of the device.

FIG. 3 shows a variation of a filter device 100 having a collar comprising a lasso-type mechanism that can adjust a diameter of a portion of the device 100. As shown, the filter device 100 can include a proximal lasso 152 and/or a distal lasso 154. Each lasso can be independently adjusted using one or more wires 156, 158 that are extended through the guide sheath 112. In the illustrated variation, each lasso member 152, 154 is shown to include two pull wires. However, variations of the filter device 100 include a single pull wire for each lasso or more than 2 pull wires for each lasso member 152, 154. The benefit of having separate control wires for each lasso member 152, 154 is that the proximal and distal ends of the filter device 100 can be independently controlled.

Figures 4A, 4B, 4C:
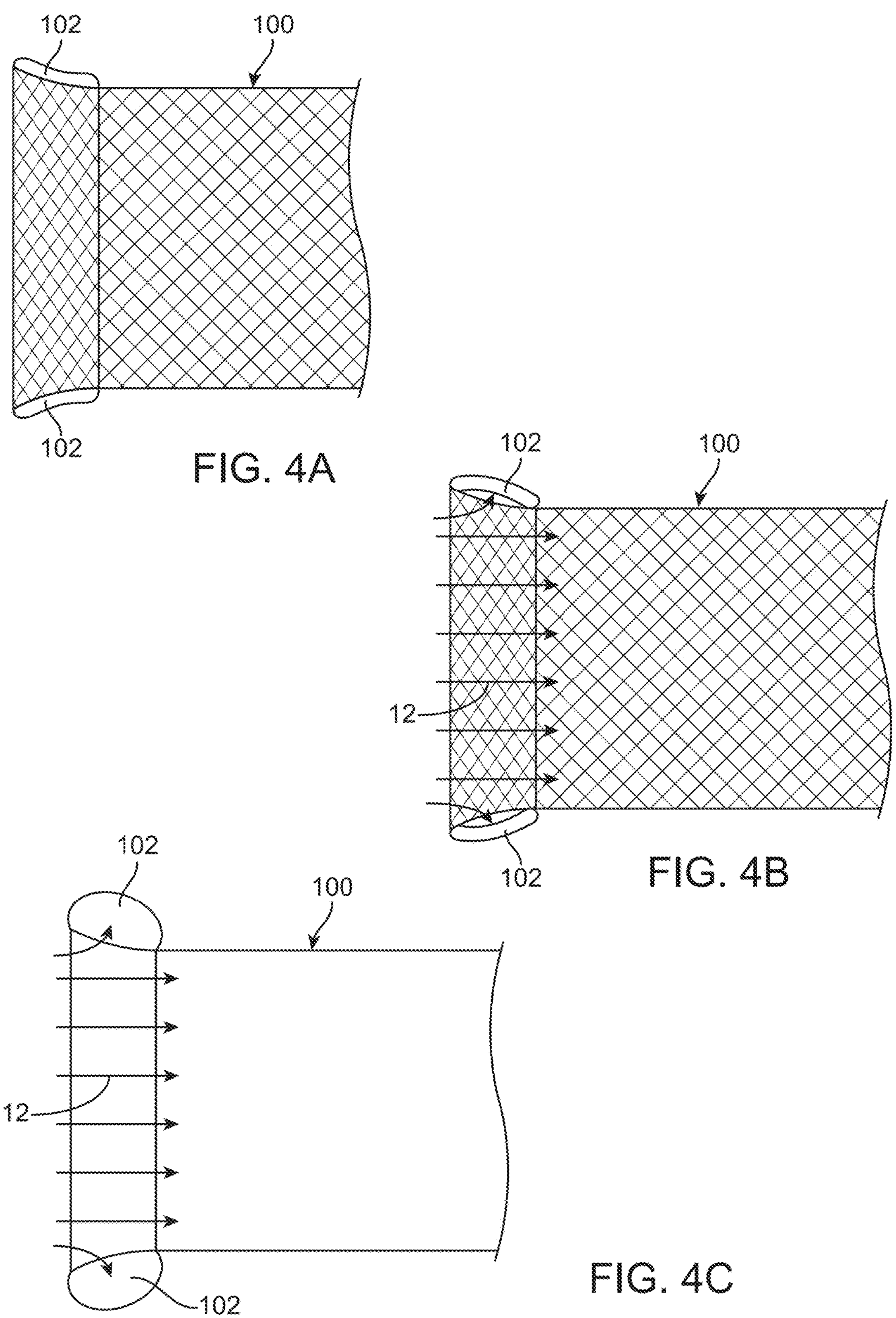
FIGS. 4A to 4I illustrate examples of flow-activated seals.

FIGS. 4A to 4C illustrate some examples of flow-activated seals 102. In one variation, the flow-activated seal 102 comprises a soft polymer membrane that can expand in response to the pressure caused by the blood flowing against the membrane. The pressure causes deflection and/or expansion of the membrane. In some variations, the flow-activated seal 102 only partially deflects and/or expands.

FIG. 4A shows a variation of a device 100 having a polymer layer that forms the flow-activated seal 102. As shown in FIG. 4B, the flow of blood 12 causes expansion and/or deflection of the membrane 102, which creates increased surface contact with the inner wall of the vessel (not shown). Variations of the flow-activated seal can simply unfold from the body of the filter device. Alternatively, or in combination, the flow-activated seal (e.g., a center portion that is not attached to the filter body) can stretch or expand upon receipt of the flow of blood. In an additional variation, the flow-activated seal is flow impermeable such that the flow against the seal increases pressure at the seal. In addition, the flow-activated seal typically comprises a softer, more compliant material as compared to the mesh of the filter device. This difference allows the flow-activated seal to conform to any irregularities on the vessel wall. This allows the filter device to form an improved seal against the vessel wall. Variations of the filter devices 100 can include flow-activated seals 102 that provide increased friction when expanded/deflected against the vessel wall. For example, the membrane 102 can include a roughened surface texture or particles that increase resistance to movement of the filter device in response to the blood flow. These expandable sealing members can be distensible or non-distensible.

FIG. 4C illustrates another variation of a flow-activated seal 102 in a filter device 100, where blood flow causes the seal 102 to balloon or expand outwards from the mesh forming the device 100.

Variations of the flow-activated seal 102 membranes can be fabricated from thin-film polymer or elastomer or similar materials. A thermoplastic urethane could be very suitable, as could other thermoplastic elastomers. Variations of the devices include membranes about 0.001" in thickness. Alternatively, variations of the membranes can include thicknesses of 0.0003" to 0.003". The membranes can be processed with a "redundancy" such as folds or extra slack to further enhance the ease and size of the opening of the membrane.

Figure 4D:
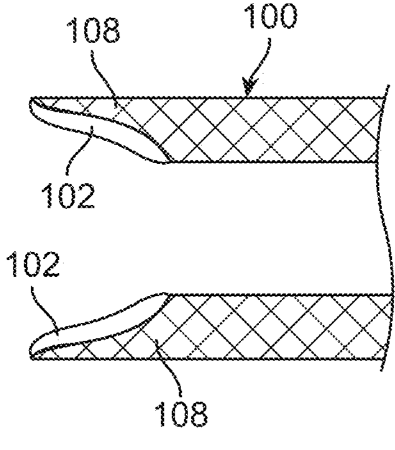
Figure 4E:
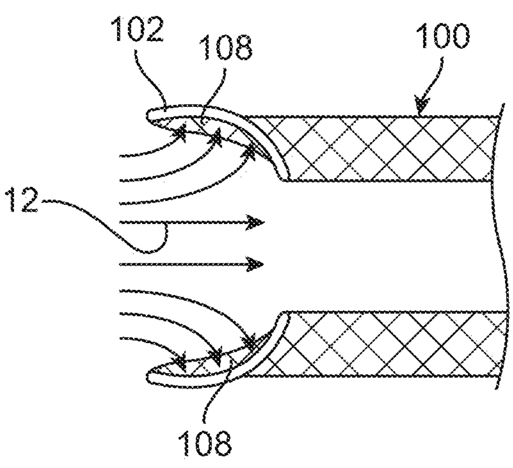

FIG. 4D to 4G illustrate additional configurations of a flow-activated seal 102. In FIG. 4D, the flow-activated seal comprises an elastic polymer positioned on the interior of a braid structure, forming the filter device 100. As shown in FIG. 4E, as blood flow 12 enters the filter device 100, the blood flow 12 deflects/displaces the polymer material along with a portion of a mesh 108, forming the filter device 100. Therefore, the blood flow 12 forces the polymer and mesh 108 to expand and form a seal against the vessel wall.

Figure 4F:
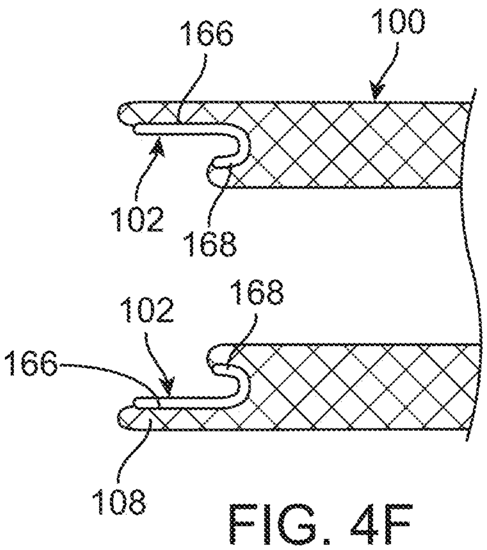
Figure 4G:
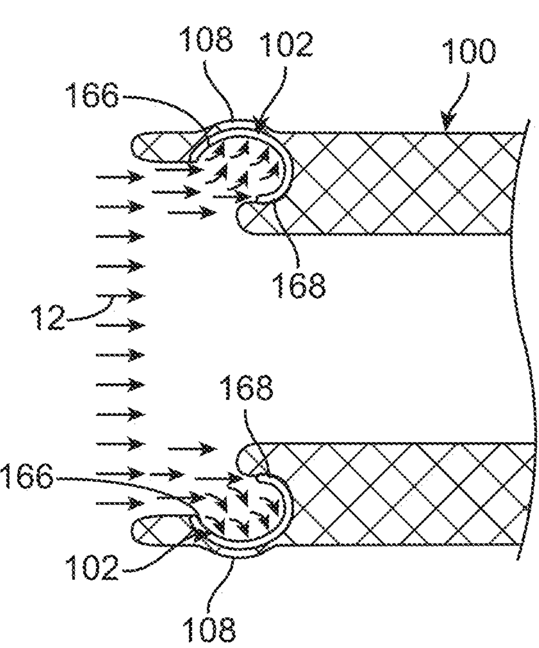

FIG. 4F illustrates another variation where the polymer layer or membrane is located within a filter device 100. As shown, a soft, ultra-compliant polymer (such as urethane or another thermoplastic elastomer, TPE) forms a shape within the filter device 100 that captures blood flow 12 using a dual-layer configuration that includes an upper seal surface 166 and a lower seal surface 168 that functions as a flow-diverting surface. The seal 102 shown in FIG. 4F, for example, includes a large upper sealing surface 166 adjacent to an outer surface of the filter device 100 and a smaller lower sealing surface 168 adjacent to an inner passage of the filter device 100. As blood flows into the space between the upper 166 and lower 168 sealing surfaces, the pressure inside (i.e., between the two surfaces) increases in fluid pressure, which helps the seal 102 to advance outward against the vessel, as shown in FIG. 4G. In one variation, the lower sealing surface 168 is intentionally smaller than the upper to ensure that the upper surface 166 expands more than the lower surface 168. However, alternate variations permit design selection to allow the upper surface 166 to expand less than the lower surface 168. As shown in FIG. 4G, the blood flow 12 enters the membrane 102 to cause deflection and displacement such that the filter device 100 seals against the arterial wall.

Figure 4H:
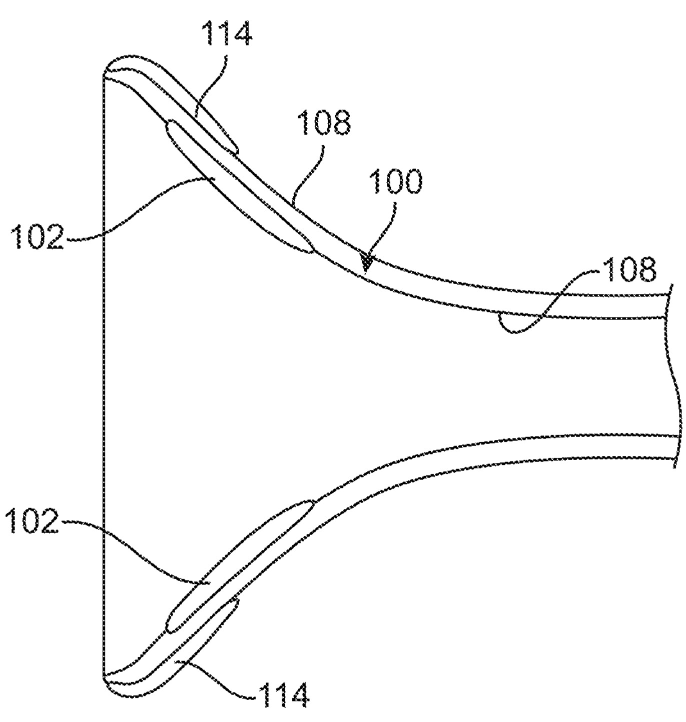
Figure 4I:
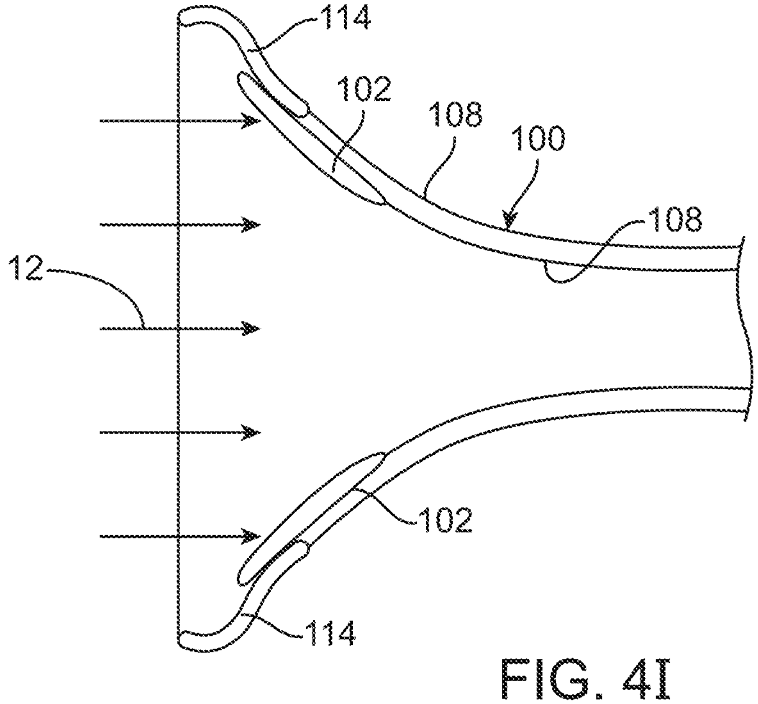

FIGS. 4H and 4I illustrate a variation of a filter device 100 having a first flow-activated seal 102 with a secondary seal 114. In this variation, the flow-activated seal 102 is located within the filter device 100, while the secondary seal 114 is located on an exterior of the device 100. Since layers 102 and 114 are affixed to the two layers of the mesh filter 108, when blood flows 12 (as shown in FIG. 4I), the flow 12 increases the pressure on the surface of the inner membrane 102 to deflect and push on the outer membrane 114. The two membranes, 102 and 114, form a seal at the area where they overlap. This configuration comprises two separate seals, 102 and 114, that function as a single seal or single layer.

While the variations of the flow-activated seal discussed herein are shown in relation to the distal portion of the filter device, additional variations of filter devices include flow-activated seals on the proximal region of the filter device as well. Such a proximal flow-activated seal can further assist in sealing the filter device against the guide catheter or other device advanced therethrough. In such cases, the design of the proximal flow-activated seal will be actuated by blood flowing into the distal portion, through the filter device, and toward the proximal portion.

Figure 1A:
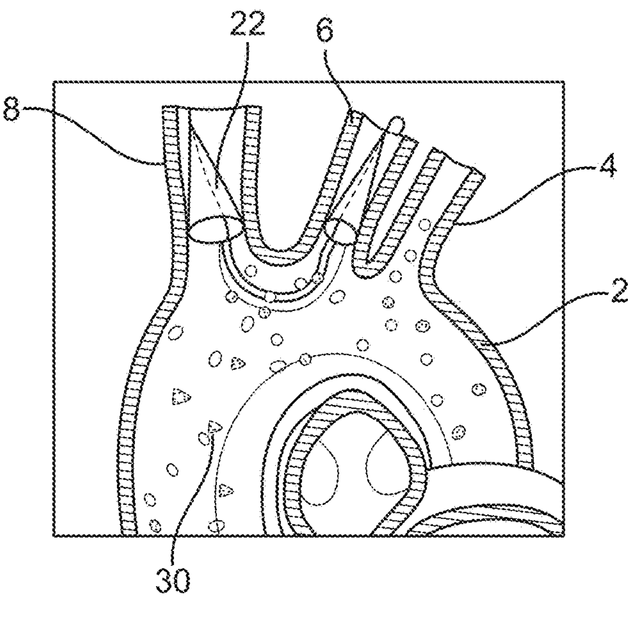
FIGS. 1A to 1C show examples of conventional vascular protection devices.
Figure 1B:
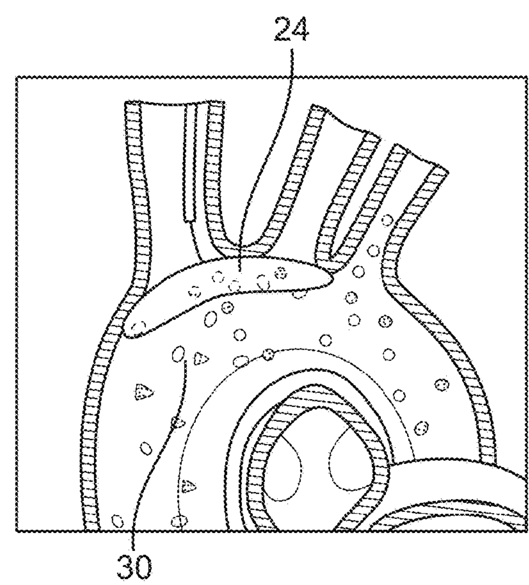
Figure 1C:
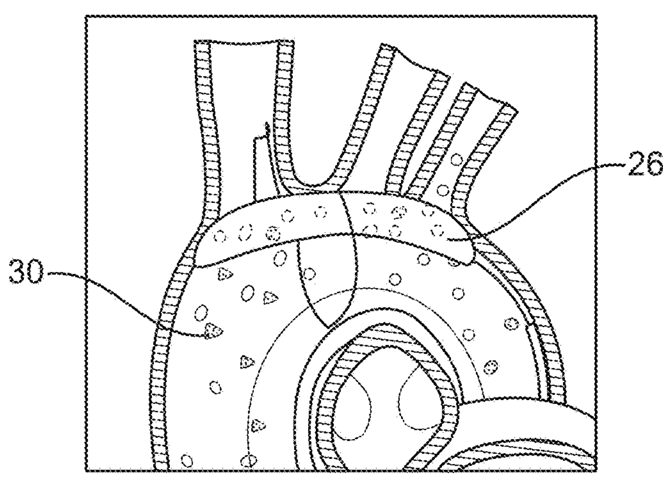
Figure 5A:
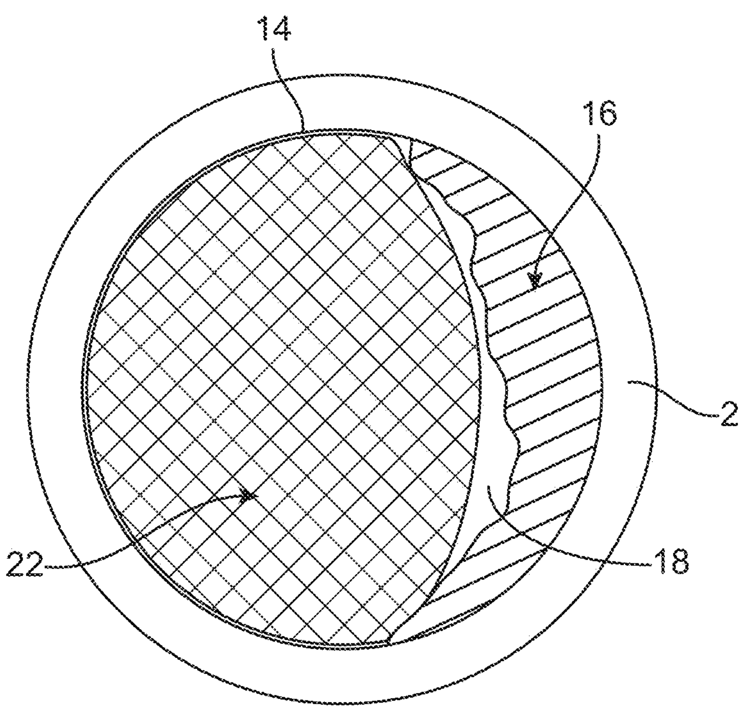
FIG. 5A illustrates a conventinaFIG. 5A illustrates a conventionaFIG. 5A illustrates a conventinaFIG. 5A illustrates a conventional capture device expanded against a wall of a vessel.
Figure 5B:
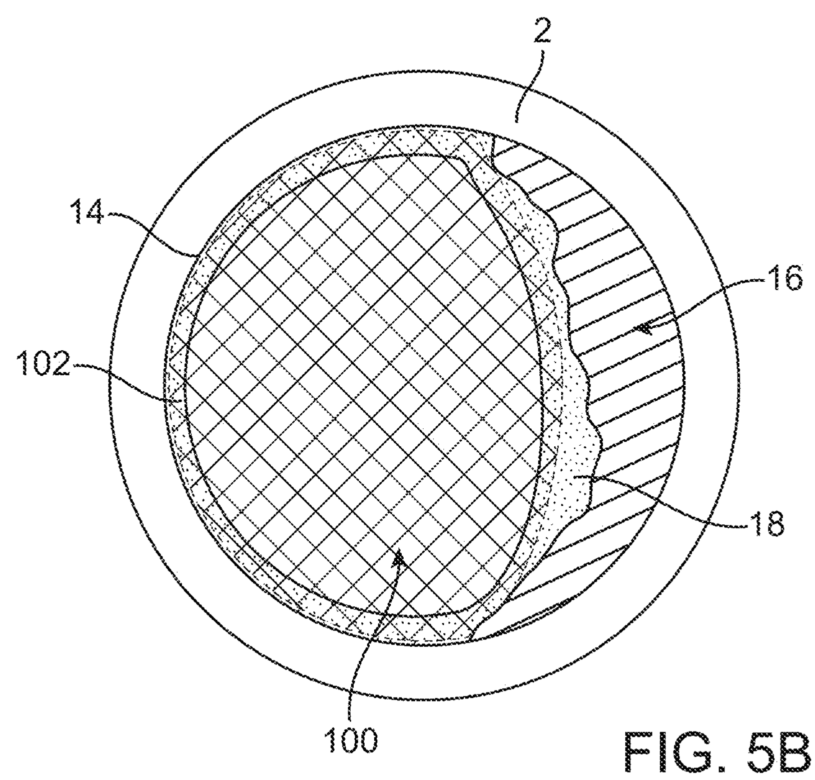
FIG. 5B illustrates an improved filter device with a flow-activated seal expanding against the wall of a vessel.

The flow-activated seal provides a significant advantage when used in a protection device by decreasing the likelihood that an embolic particle will bypass the device. FIGS. 5A and 5B illustrate the difference between conventional devices (such as those shown in FIGS. 1A to 1C) and the improved filter devices 100 discussed herein. FIG. 5A illustrates a cross-sectional view of a vessel 2 (the scale of the drawing is adjusted to better illustrate the fit of the device 22 against a wall 14 of the vessel). As shown, the perimeter of the device 22 is intended to form a seal against the vessel wall. However, irregularities 16 in the vessel 2 (such as plaque, calcification, shape of the vessel, or other naturally occurring formations) result in irregular geometries 18 that cannot be sealed with the protection device. FIG. 5B illustrates a feature of the flow-activated seals 102 of the present disclosure where the seal often has a softness or conformability that is greater than the mesh structure forming the device 100. This feature allows the flow-activated seal 102 to expand or deform into any irregularities 18 in the vessel 2 to a greater degree than the mesh or filter device 100. This creates an improved seal between the wall 14 of the vessel 2 and the filter device 100 to improve filtering of emboli within the bloodstream with an enhanced seal.

Figure 6A:
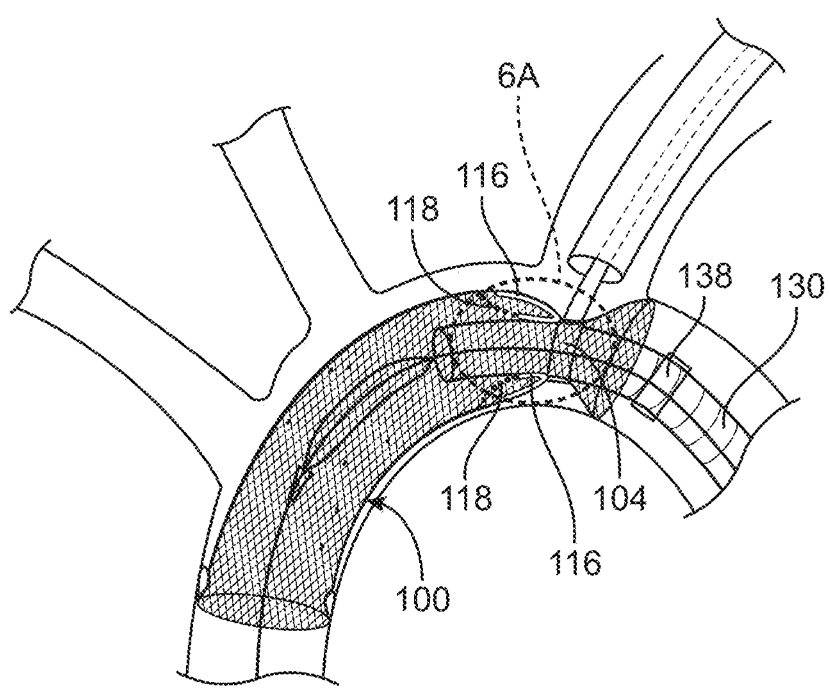
FIGS. 6A and 6B show a variation of a device having a proximal flow-activated seal that is located at a proximal region of the filter device.
Figure 6B:
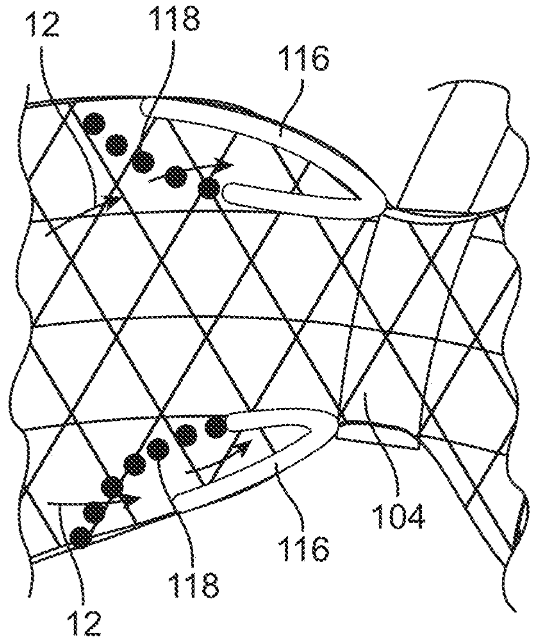

FIGS. 6A and 6B show a variation of a device having a proximal flow-activated seal 116 that is located at a proximal region of the filter device 100, much like the distal seal. Note that the collar is shown as being adjacent to the seal 116. However, variations of the filter device 100 can include a proximal seal 116 located in any part of the proximal portion. Any one of the seal designs disclosed herein for the distal seal could also be used at the proximal location, or some combination thereof as long as they seal flow from the distal portion of the device.

FIGS. 6A and 6B also show a variation where the proximal seal 116 includes an attachment 118 that connects the seal back to the braid. This connection prevents inversion of the seal 116. In the illustrated variation drawing, the seal 116 is permanently fixed to the braid where shown (i.e., adhesive bonded, thermal-mechanical encapsulation, etc.). To ensure the opposite end of the seal does not invert, either from blood flow 12 or from withdrawing the guide catheter, the seal can be additionally tethered 118 to another region of the braid. Tethering can be accomplished with a tack melt, additional encapsulation/thermal fuse, or using additional fibers or polymer, or metal filaments.

Another variation of the system can include an enhanced TAVR guide catheter 130 in a manner that enhances the sealing properties of the filter. A geometric "bump" or protrusion 138 could be on the OD of the guide 130 in the sealing region. In the variation shown in FIG. 6A, the protrusion 138 is shown outside of the filter device 100 for illustrative purposes. The protrusion 138 can be manufactured into the catheter 130. Alternatively, or in combination, the protrusion can be added to the TAVR guide catheter 130 in the sterile environment (such as a small sterile sleeve). Additionally, a swellable coating, such as a thick hydrophilic coating, could also perform a similar effect of increasing the proximal seal.

Figures 7A, 7B, 7C:
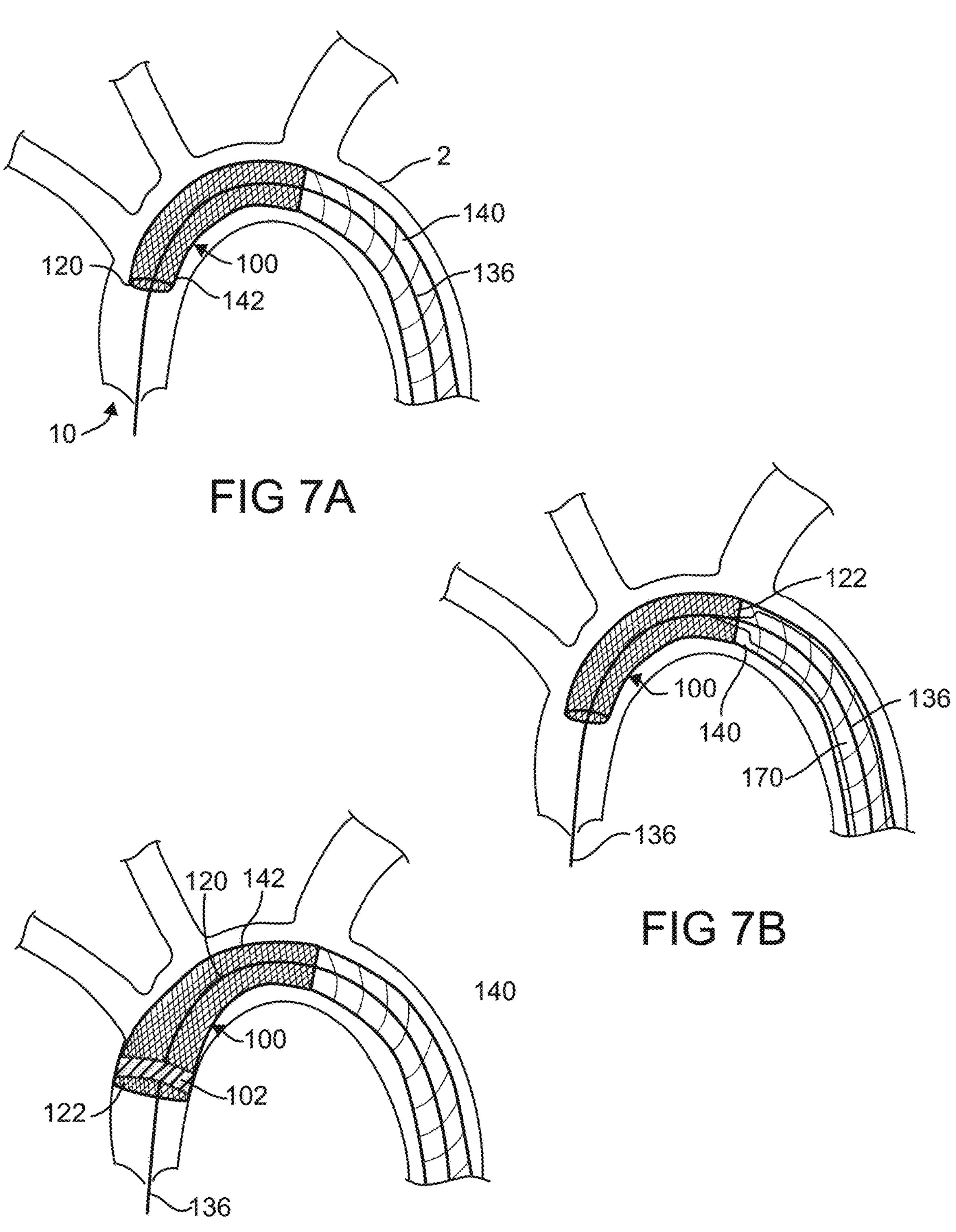
FIGS. 7A-7G illustrate an additional variation of a filter device that is integrated with a system that is delivered from the femoral artery through the aortic arch.

FIGS. 7A-7G illustrate an additional variation of a filter device 100 that is integrated with a system that is delivered from the femoral artery through the aortic arch 2 to the valve 10. In this variation, the filter device 100 is integrated and permanently fixed to a guide catheter 140. FIG. 7A shows an example of a variation of a system with a filter device 100 integrated with a guide catheter or sheath 140 that is advanced to a deployment site within a vessel 2. In this variation, the filter device 100 is inverted within the guide sheath 140, and where a proximal end of the device 120 is affixed to a distal end 142 of the guide catheter 140. As shown in FIG. 7B, a stabilizing device 170 (e.g., a dilator device or support catheter) advances to the distal end 122 of the filter device 100. FIG. 7C shows a condition where the guide 140 is withdrawn while the stabilizing device 170 stabilizes the filter device 100, such that it everts into position as the guide sheath 140 is withdrawn. The stabilizing device 170 can also be used to ensure the filter is fully reverted into an open or deployed shape by extending it through the filter device 100. FIG. 7C shows the distal portion 122 of the device 100 with a flow-activated seal and the proximal portion 120 of the device 100 coupled to the distal end 142 of the guide catheter 140.

The use of a stabilizing device 170 allows for either "extruding" of the filter by using the stabilizer/dilator 170 to push the filter 100 distally. Alternatively, the stabilizer/dilator 170 could be advanced to the inverted filter at the proximal end to stabilize the filter, and then an outer sheath constraining sheath could be withdrawn proximally to unsheath the filter.

Figure 7D:
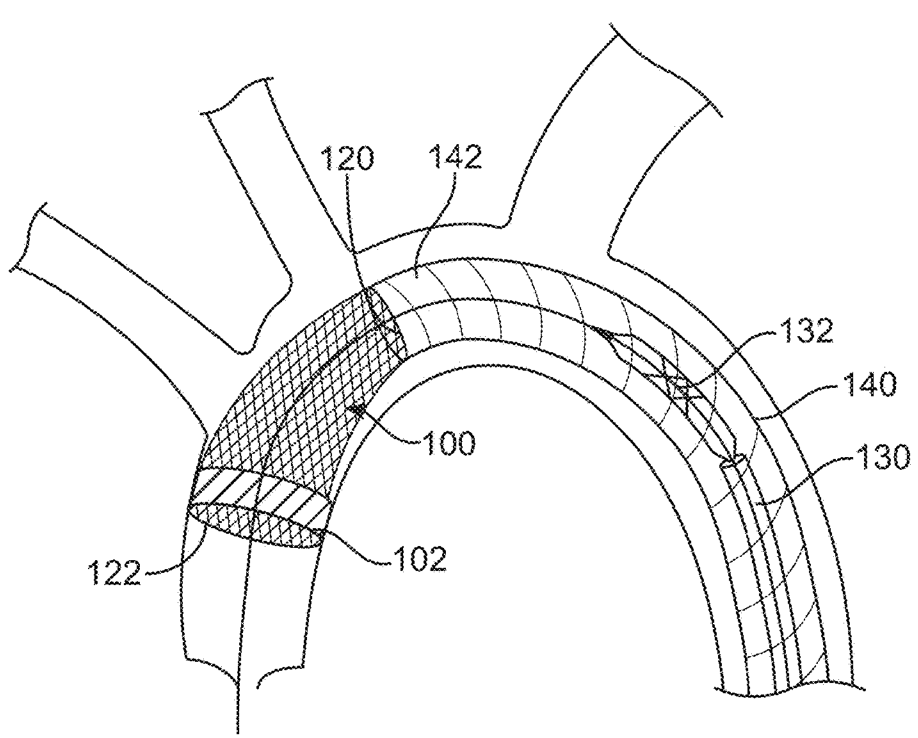
Figure 7E:
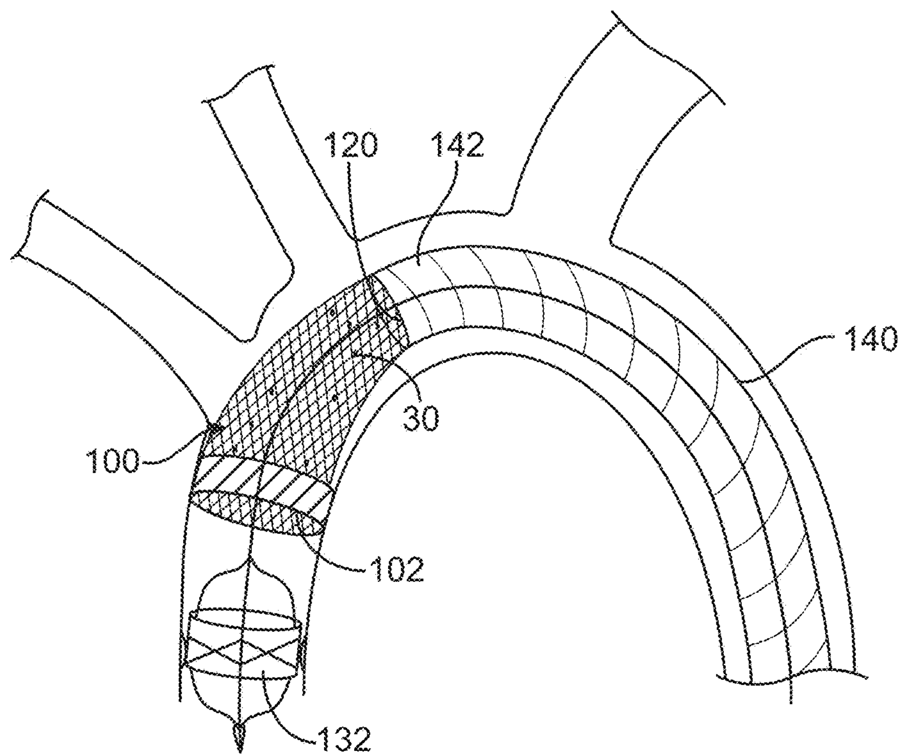

Next, as shown in FIG. 7D, the TAVR implant 132 and system 130 advance through the guide catheter or sheath 140 with the integral filter device 100. The distal end 122 of the filter 100 contains the flow-activated seal 102. FIG. 7E illustrates the TAVR implant 132 deployed at a deployment site with emboli 30 in the flow of blood, but is directed into the filter device 100 because of the flow-activated seal 102. There is no risk of the emboli escaping through the proximal end 120 of the device 100, since the proximal end is integral with the distal end 142 of the guide catheter 140.

Figure 7F:
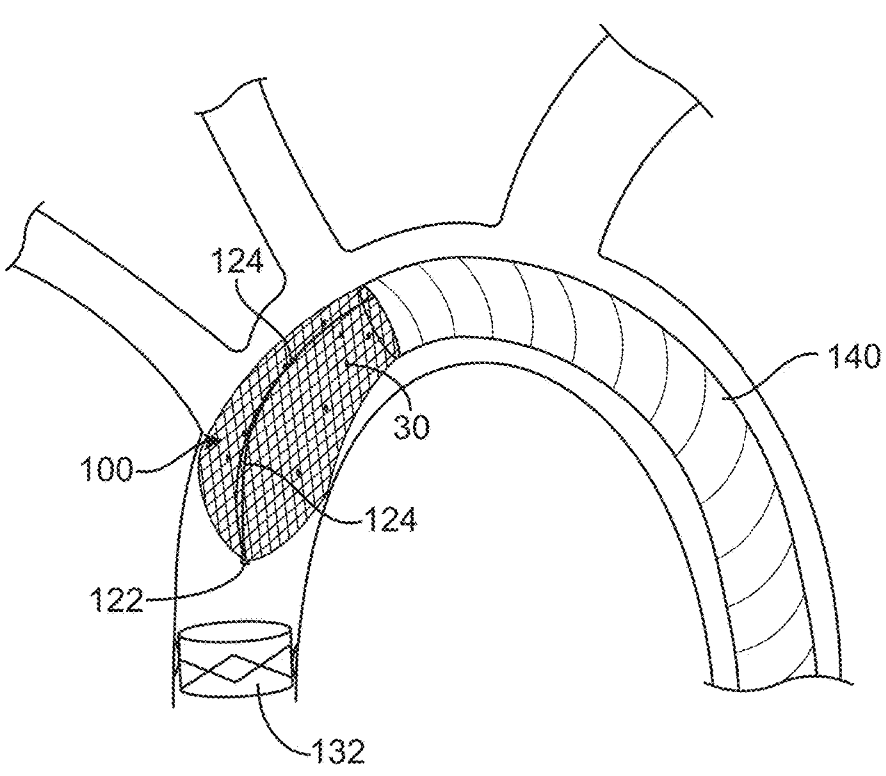
Figure 7G:
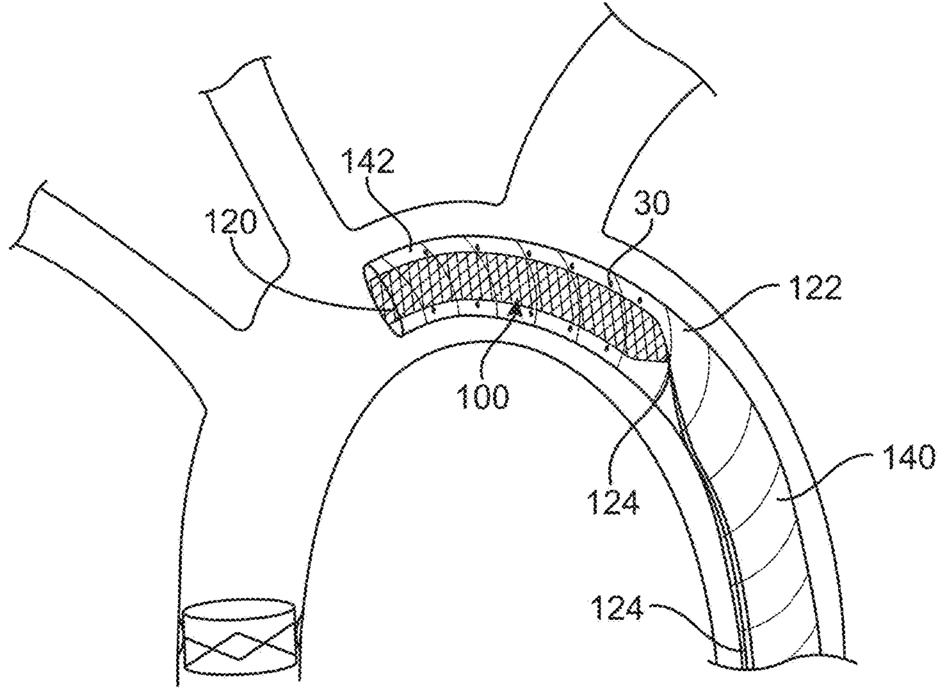

FIG. 7F illustrates closing of a distal end 122 of the filter device 100 using one or more pull wires 124. As illustrated, the embolic particles 30 are secured within the closed filter device 100 that is integral/secured to the guide catheter 140. FIG. 7G illustrates an optional feature of the system where the filter device 100 can be inverted back into the guide catheter 140. As shown, the pull wires 124 are tensioned to bring the distal portion 122 of the closed filter device 100 back into the catheter body 140, which causes inversion of the filter device 100 into the guide body 140. Again, there is no risk of losing captured emboli since the filter is closed. Such a step could ensure filter and emboli are protected during removal from the body.

It should also be noted that additional design options include building the filter onto the femoral introducer sheath (i.e., a long sheath with the filter located near the aortic valve) or using a long sheath to constrain the filter if it is not pre-inverted in the guide catheter.

Figures 8A, 8B, 8C:
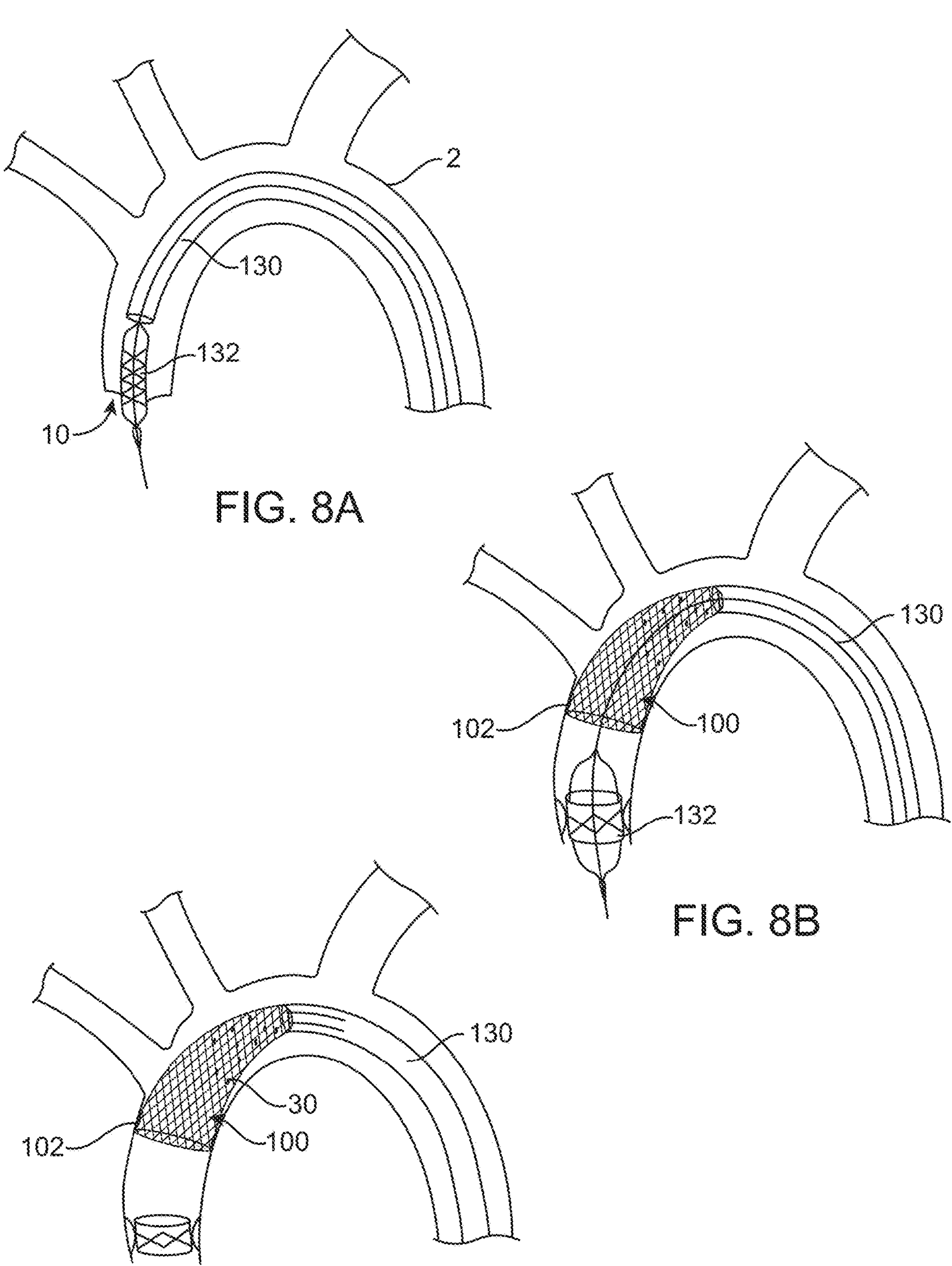
FIGS. 8A to 8E show another variation of a filter device incorporated directly into the procedural device.

FIGS. 8A to 8E show another variation of a filter device incorporated directly into the procedural device. For example, the filter device can be built directly into the TAVR guide catheter, which eliminates the need for an additional guide catheter for the filter alone. FIG. 8A illustrates a TAVR guide catheter 130 that is used to advance the TAVR implant 132 to the site of the valve 10 within the aorta 2. FIG. 8A does not show the filter but is loaded inside the TAVR guide catheter 130.

Figure 8D:
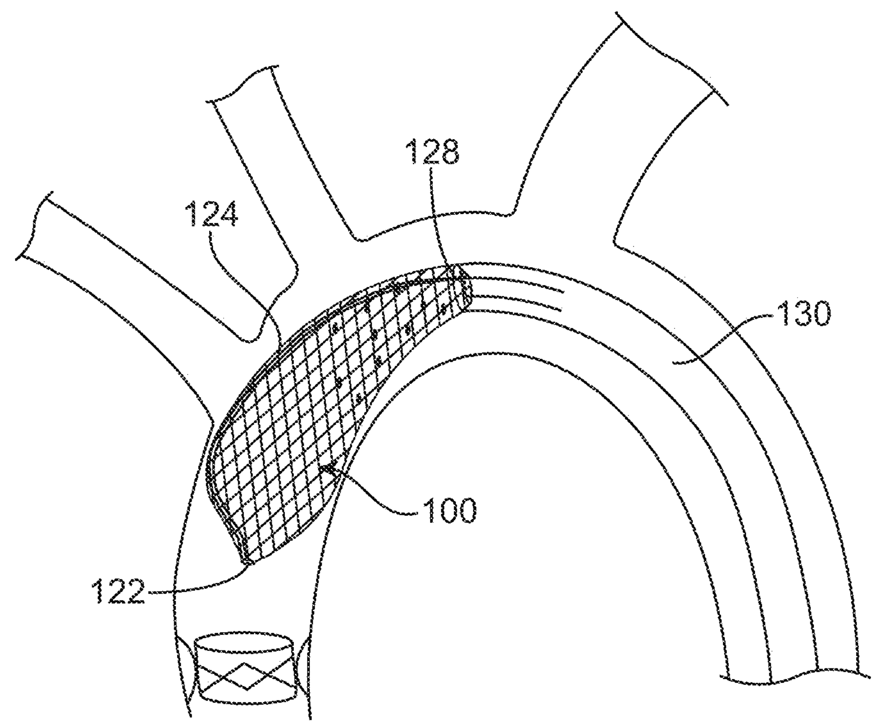
Figure 8E:
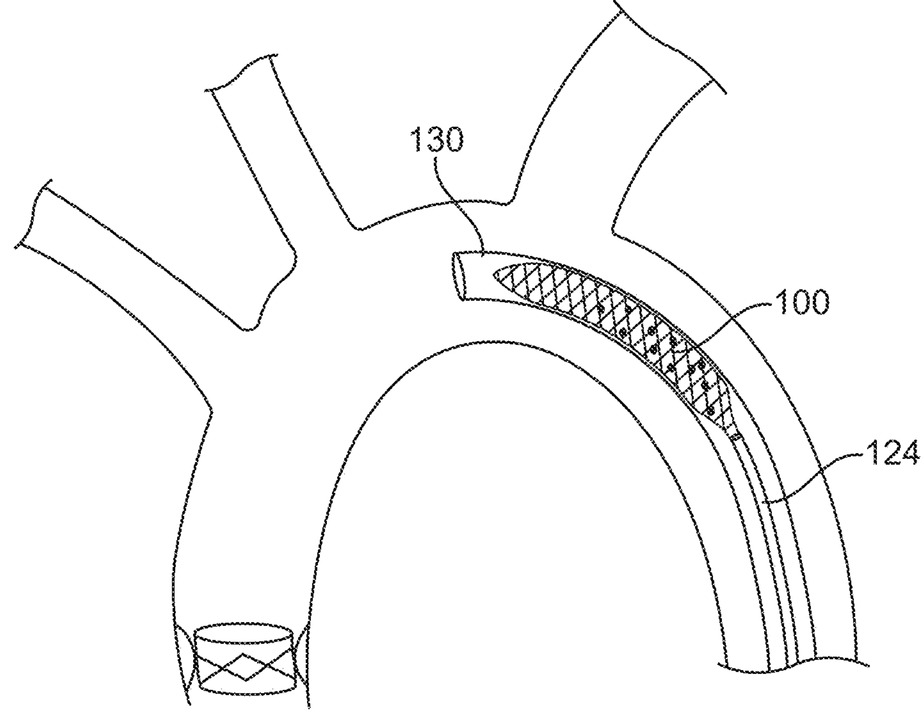

FIG. 8B shows the filter device 100 delivered from the TAVR guide catheter 130. This deployment can be accomplished in any of the ways disclosed herein (inverted inside the guide catheter and delivered by 'pushing' with another integrated tube or similar, or simply compressed within the TAVR guide catheter and unsheathed). FIG. 8C shows the TAVR balloon and guidewire removed from the site. Since the filter device 100, is mechanically integratted into the catheter body 130, there is no concern that emboli can escape through the proximal region of the filter device 100. FIG. 8D illustrates one or more guidewires 124 that are used to close a distal end 122 of the filter device 100. The proximal end of the filter device 100 is positioned within the distal end 128 of the TAVR guide catheter 130. FIG. 8E illustrates a variation where the filter device 100 is coupled to be slidable within the TAVR guide catheter 130, which allows the closed filter to be brought back into the guide lumen while being removed.

The variations shown in FIGS. 7A-7G and 8A-8E are systems that can be constructed either into a delivery guide catheter of the TAVR system or into a separate delivery catheter.er of the TAVR system or into a separate delivery catheter.er of the TAVR system or into a delivery catheter.

Figure 9A:
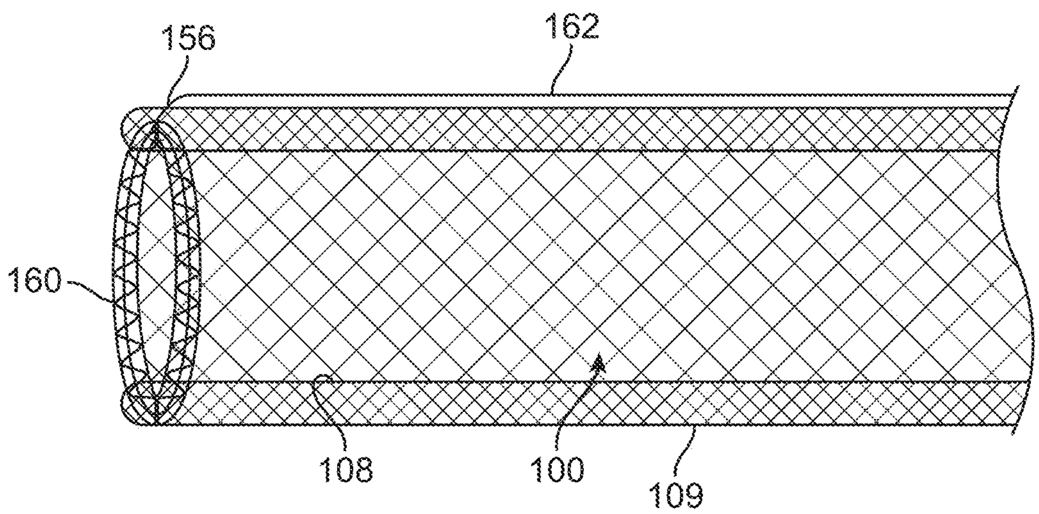
FIGS. 9A to 9C illustrate additional configurations for restricting one or both ends of the filter device.
Figure 9B:
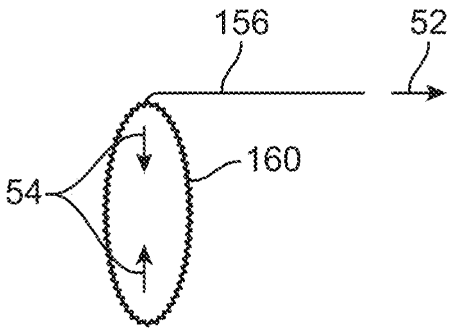
Figure 9C:
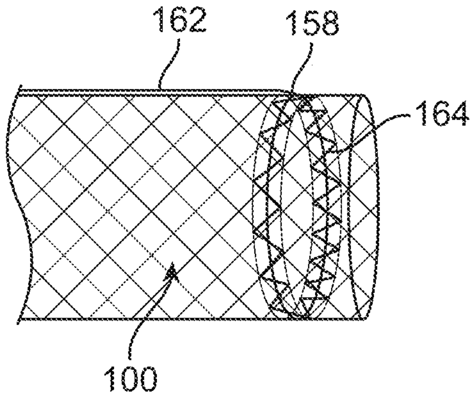

FIGS. 9A to 9C illustrate additional configurations for restricting a filter device 100. In the example shown in FIG. 9A, the filter device 100 comprises a double mesh layer with an inner mesh 108 and an outer mesh 109. In one examplee example, the mesh layers 108, and 109 comprise Nitinol braids. An additional ring structure 160 is provided at the end of the filter device 100. In the illustrated example, the ring structure 160 comprises a coil shape. However, alternative shapes (e.g., straight wire, sinusoidal, helical, etc.)

can be used as long as the shape provides an outward radial force to maintain the end of the filter 100 in an open configuration. One or more pull wires 156 are coupled to the ring 160 such that the application of a force on the pull wire 156 closes the ring 160 and the end of the filter device 100. The illustrated example shows the pull wire 156 extending through a tube (e.g., a polyimide tube). FIG. 9B shows a ring structure 160 coupled with a pull wire 156 without the mesh of the filter device. As noted above, the coiled ring 160 provides an outward radial force that opens the end of the filter device when unconstrained. Application of a force 52 on the wire 156 away from the ring 160 causes closure 54 of the ring 160 and the filter device.

FIG. 9C shows another variation of a self-expanding ring 164. In this variation, the ring is in an undulating shape with a pull wire 158 passing through the ring 164. As noted above, the ring 164 is self-expanding (or heat-activated) to provide an outward expanding force on the filter device 100. The pull wire 158 acts to close the ring 164 and filter device 100 upon the application of a closing force. The pull wire 158 can optionally pass through a tube 162 or can be incorporated into the mesh of the filter.

It is noted that any of the ring designs discussed herein can be used interchangeably for the distal and/or proximal regions of the filter or any combination thereof. In addition, the ring designs can be incorporated at any medial portion of the filter if required.

Figure 10A:
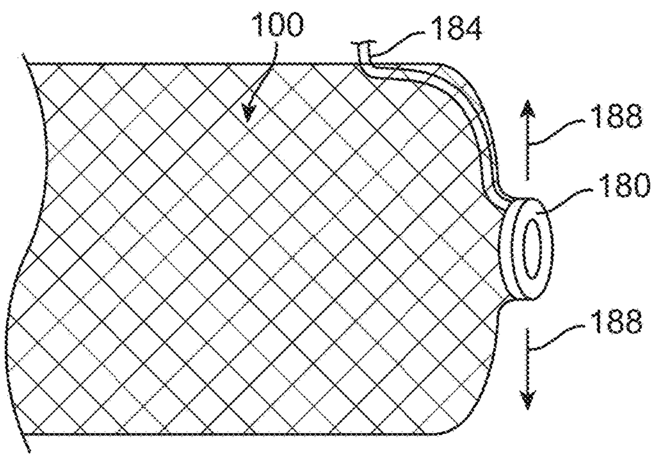
FIGS. 10A to 10C illustrate the use of one or more balloons that control an opening of a filter device.
Figure 10B:
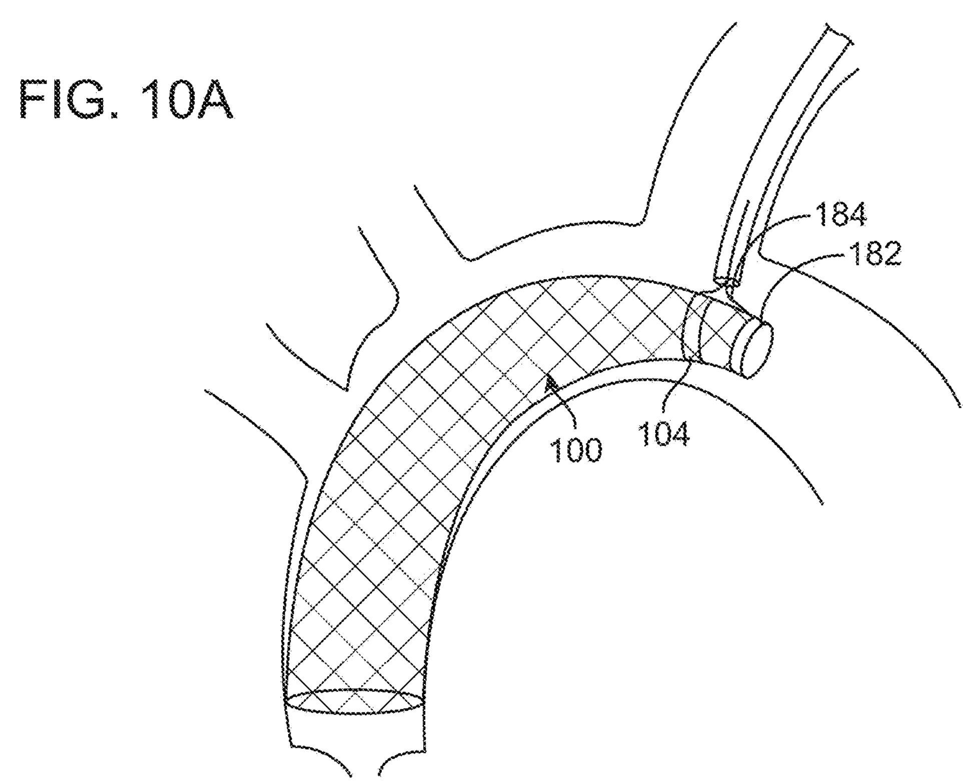
Figure 10C:
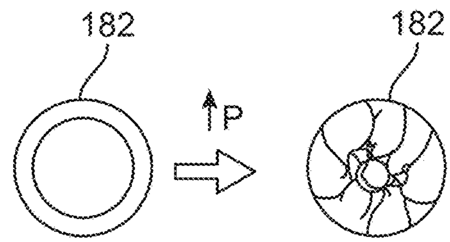

FIGS. 10A to 10C illustrate the use of one or more balloons that control an opening of a filter device 100. For example, FIG. 10A illustrates a variation of a filter device 100 having an elastomeric balloon 180 at the end of a filter device 100. In this variation, the balloon is in a closed position (as shown) when not pressurized. Application of a fluid through a line 184 causes the balloon 180 to expand 188 to open the filter device 100. FIG. 10B illustrates another variation of a filter device 100 having a balloon 182 that is in a normally open position. Application of fluid through line 184 causes the balloon 182 to collapse inwards, as shown in FIG. 10C.

Figure 11A:
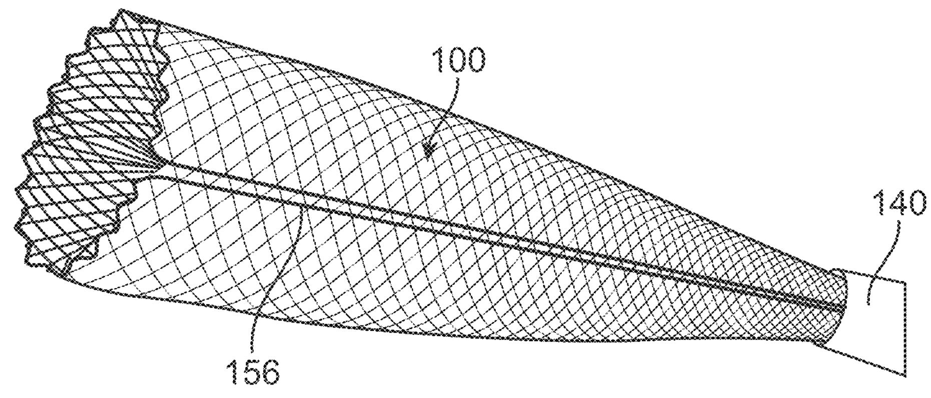
FIGS. 11A to 11C illustrate an additional variation of filter devices that use a lasso effect to close an end of the filter.
Figure 11B:
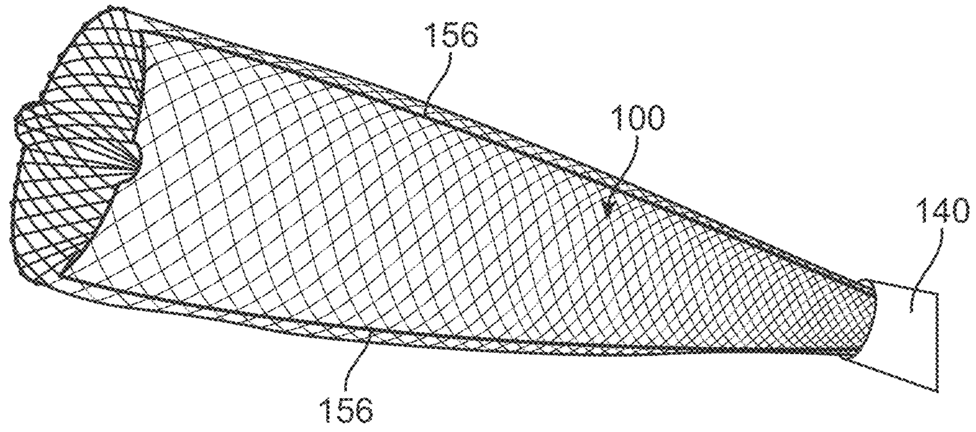
Figure 11C:
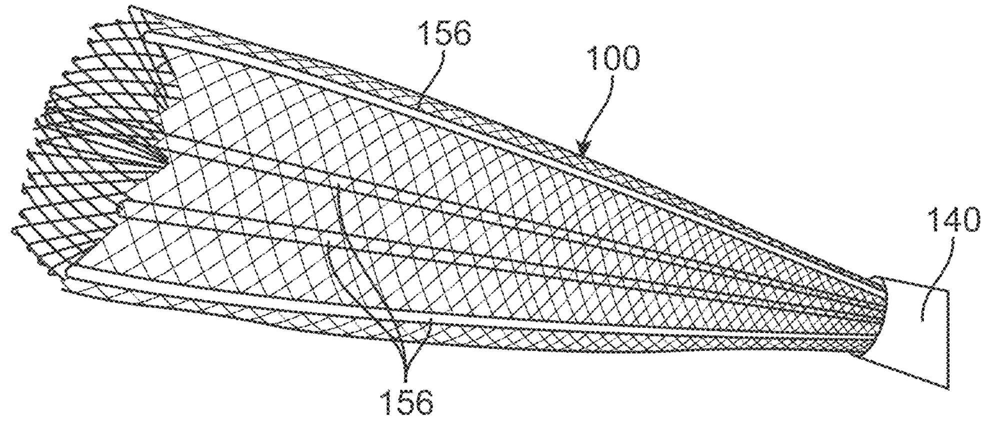

FIGS. 11A to 11C illustrate an additional variation of filter devices that use a lasso effect to close an end of the filter. Again, all of the closing mechanisms discussed herein can be applied to a proximal, distal, and/or medial portion of the filter device. FIG. 11A shows a pull wire 156 used to create an aperture or opening at an end of the filter device 100 that can be restricted/occluded by pulling on the wire 156. Pulling the wire 156 reduces the diameter of the filter device 100 and effectively closes the attached portion of the filter 100. In this variation, the wire 156 is located at the distal end of a guide catheter 140 with an integrated filter device. However, this closing structure can be used on any filter device. In addition, these concepts can apply equally to the proximal end of a filter as well.

As noted above, in order to prevent the spreading of emboli, some applications of the device require the closing mechanism to completely and fully close off the open end of the filter. In such applications, the wire 156 can be constructed from a superelastic nitinol wire with an oxide coating, about 0.001" to 0.002", but variations of the device allow for up to 0.010". The wire could also be ribbon wire, rectangular, or other shape. Fiber, polymer, or thread are also options. FIG. 11B shows two sets of pull wires 156 coupled to the distal end of the filter device 100. FIG. 11C shows multiple sets of pull wires 156 that close the end of the filter device.

Figure 12A:
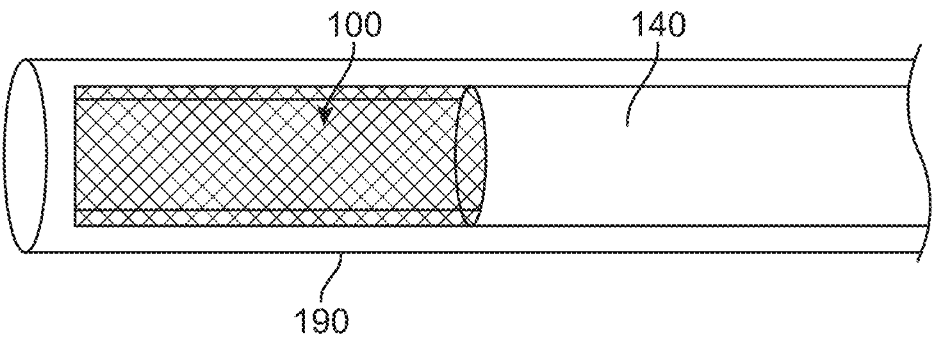
FIGS. 12A to 12C illustrate another variation of a filter device that is integrated with a guide catheter and constrained within an outer sheath.
Figure 12B:
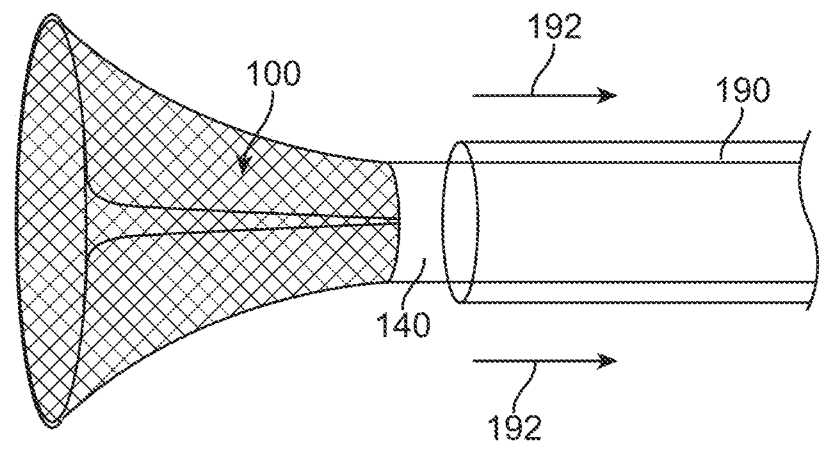
Figure 12C:
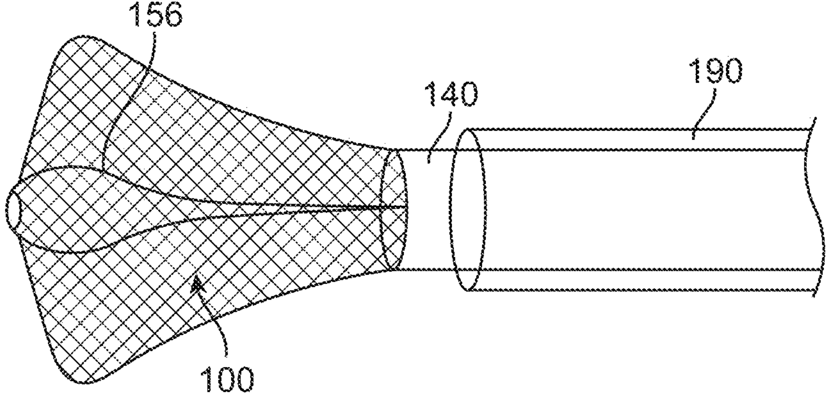

FIGS. 12A to 12C illustrate another variation of a filter device 100 that is integrated with a guide catheter 140 and constrained within an outer sheath 190. FIG. 12A shows a filter device 100 and guide catheter 140 constrained within an outer sheath 190 so that the system can be advanced to a deployment site, as discussed herein. This variation is typically delivered from the femoral artery, where the TAVR system is delivered. FIG. 12B shows the outer restraining sheath 190 being withdrawn 192 while the guide catheter 140 is held stationary. Withdrawing the constraining sheath 190 causes the filter device 100 to expand. As noted above, the flow-activated seals will ensure proper filtering of the vessel. This is a two-catheter design, or coaxial system, where one catheter 140 is integrated with the filter device 100, and one catheter/sheath 190 acts to constrain the filter 100 for delivery. Variations of the system include replacing the outer sheath 190 with another mechanism, such as a coil or short collar, to constrain the filter. In additional variations, the outer sheath 190 could be very thin, such as a coil-reinforced polyimide tube, in cases where it is only intended to constrain the filter and does not need to navigate on its own. FIG. 12C shows activation of the pull wire 156 after completion of the procedure. Activation of the pull wire closes the end of the filter device 100 to secure any embolic particles within the filter 100.

Figure 13A:
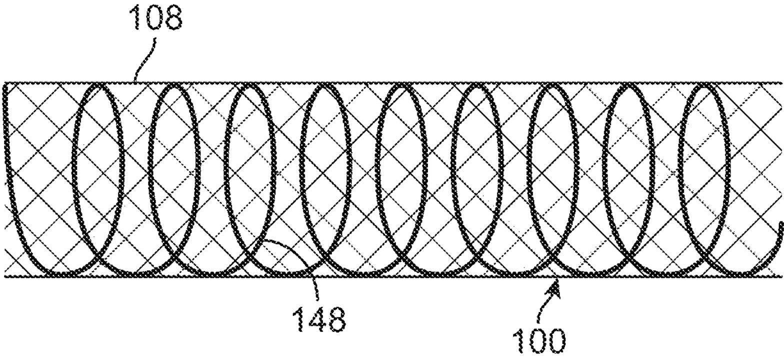
FIGS. 13A to 13C illustrate variations of a filter body for use with the devices described herein.
Figure 13B:
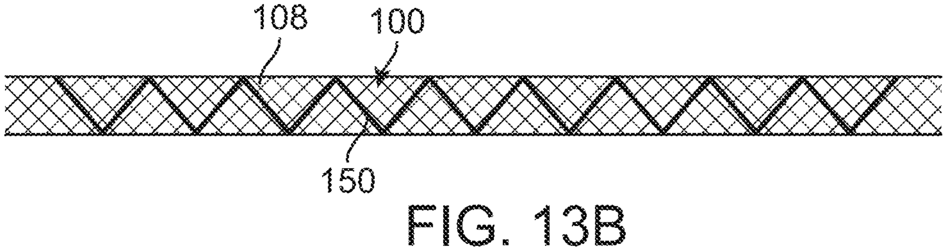
Figure 13C:
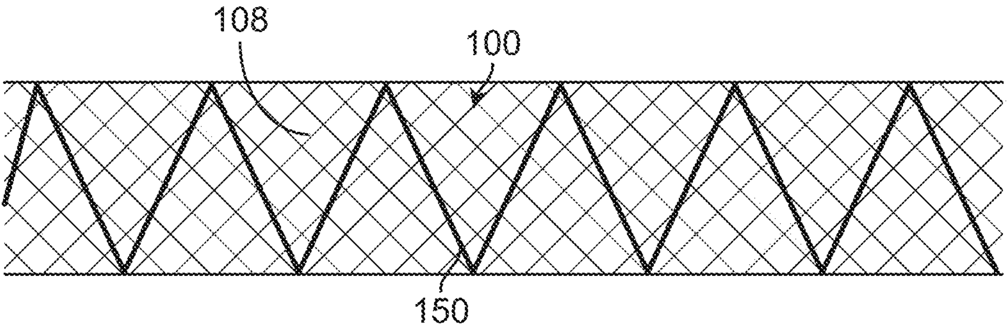

FIGS. 13A to 13C illustrate variations of a filter body for use with the devices described herein. FIG. 13A shows a dual-layer filter device 100 with the outer layer comprising a mesh 108 or a thin film porous material, such as a polymer film with holes or pores (e.g., laser-drilled, chemically formed, mechanically formed) and the inner layer comprising a coil or braid 148 that is designed for providing radial force such that the filter body 100 expands with radial force to contact the wall of the vessel. FIGS. 13B and 13C, respectively, illustrate a non-expanded and expanded filter device 100 comprising an inner inflation member 150 with a mesh or braid 108. The coiled inflation member 150 expands and opens the braid upon inflation. It should also be noted that filter device 100 can be made from components other than wire braid or mesh. For example, the filter device 100 can comprise a porous polymer film, such as polyurethane or a similar material. The porosity of the film can be achieved with laser processing, chemical etching or other chemical treatment, or micro-abrasion processes, or other means known to those skilled in the art. In another variation, the filter device is constructed from a thin film process. The thin film, such as a thin film metal, can be made with a custom-selected porosity. The filters shown in FIGS. 13A to 13C provide multiple layers where the inner layer (e.g., the coil, braid, stent-like structures) provides an outward radial force to open the filter and the outer layer (e.g., braid, polymer, porous film, porous metal film) provides the filtration for blood.

FIGS. 14A to 14E show another variation of a filter device with a multi-layer seal. In this variation, as shown in FIG. 14A, the mesh 108 of the filter device 100 terminates in a series of petals 105, 107. The construction of the petals 105, 107 can include separate wires or wires from an inner/outer mesh that returns back to form an outer/inner mesh. The petals can be atraumatic or can include features that increase friction against the vessel wall (or wall of the body lumen). FIG. 14B illustrates alternating petals 107 being shaped with an offset 126, e.g., alternating petals 107 are shaped to extend upward 126, and then the next petal 105 can either be horizontal (as shown) or even extend slightly downward (into the ID of the device 100) as shown in FIG. 14C. This angulation and sepahe device 100) as shown in FIG. 14C. This angulation and separation of the petals create a space to attach the flow-activated seal 102. As shown, the seal 102 can have both an upper surface 164 and a lower surface 165. In one variation, the seal 102 can be formed from a single section of polymer film or could be two independent pieces that meet at the apex and are overlapped. It is also possible that selective small "holes" 163 in the seal 102 could be beneficial to control the pressure inside the seal 102 and ensure that blood flow doesn't over-pressure the seal 102 and dislodge the position of the filter device 100. It should also be noted that this same design concept could be achieved with "standard" braid (i.e., no petals). In this case, individual braid wires would be formed to either extend outward or flat/inward, and then the ends of the wires would terminate within the seal polymer. FIG. 14E illustrates a partial side view of the upper seal 164 and lower seal 165 with a space therebetween for increasing pressure in response to blood flow. As noted herein, the upper seal 164 can be configured to preferentially deflect into a wall of the vessel (e.g., via sizing or material selection).

Figure 15A:
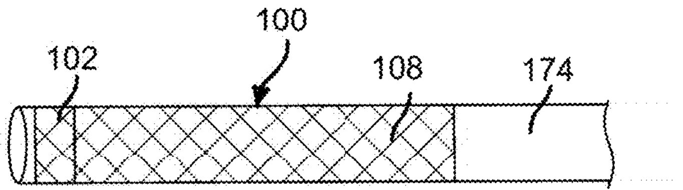
FIGS. 15A to 15E illustrate variations of a filter device configured for an exterior of a guide catheter, sheath, guidewire, and/or other devices.
Figure 15B:
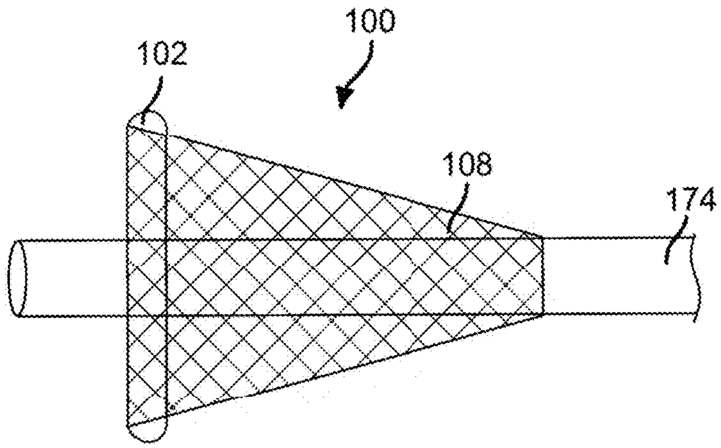
Figure 15C:
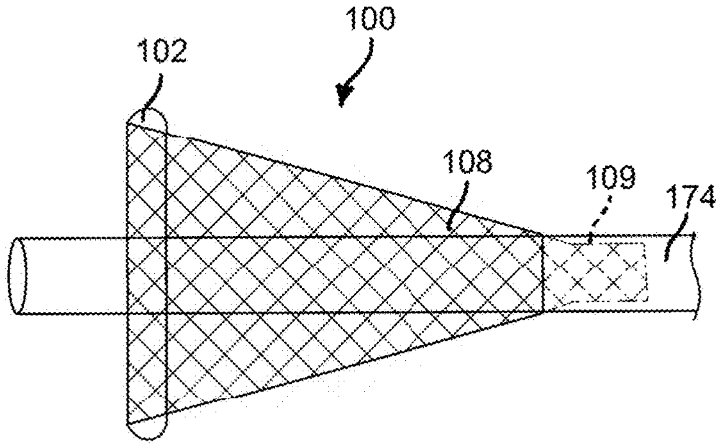
Figure 15D:
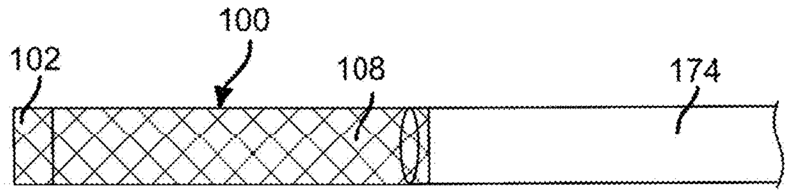
Figure 15E:
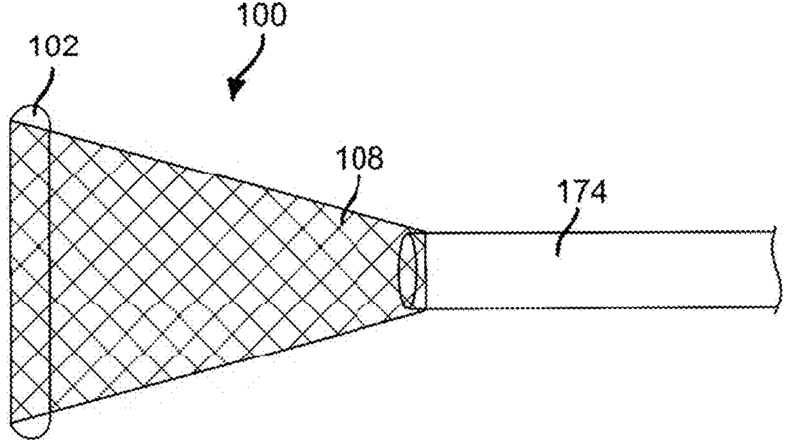

FIGS. 15A and 15D show additional variations of filter devices 100 in a pre-deployed configuration. Previous variations showed the filter device 100 attached at or near the distal end of the guide catheters. Here, the filter 100 is attached to the outside of the guide 174, which can be a guidewire, sheath, catheter, or other medical device. The filter 100 can be self-expanding (or mechanically assisted, as described before) and then opened by conventional methods (releasing pull wire, activating coil or inflation lumen, or removing external sheath or covering). Once expanded, the device 100 assumes the configuration shown in FIGS. 15B and 15D. FIGS. 15A and 15B show the filter device 100 extending from the guide device 174, while FIGS. 15D and 15E show the filter device 100 extending beyond a distal end of the guide device 174. FIG. 15C illustrates a variation similar to FIG. 15B but with a portion of the mesh 109 extending into or is embedded within the guide device 174. Once the collection of thrombi is completed, the filter 100 can be closed to the OD of the guide/sheath 174, trapping the emboli between the filter and guide surface. It should be noted that the guide 174 could be a procedural guide, TAVR guide, and/or sheath. Sheath options inccedural guide, TAVR guide, and/or sheath. Sheath options include long introducer sheath, procedural sheath, and/or expandable sheath (i.e., e-sheath).

Figure 16A:
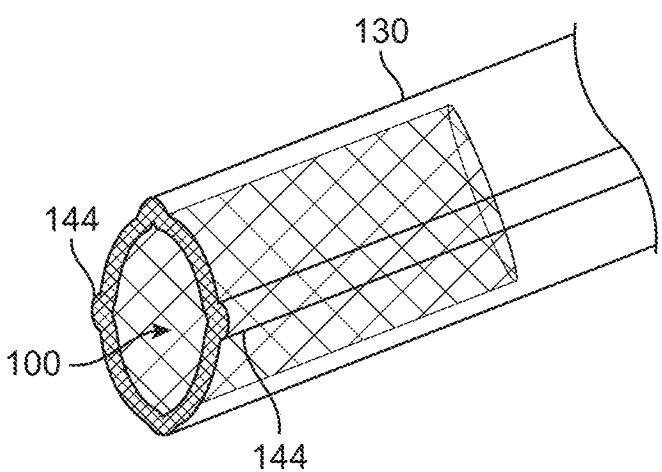
FIGS. 16A to 16C illustrate additional variations of devices for use with the procedures described herein.
Figure 16B:
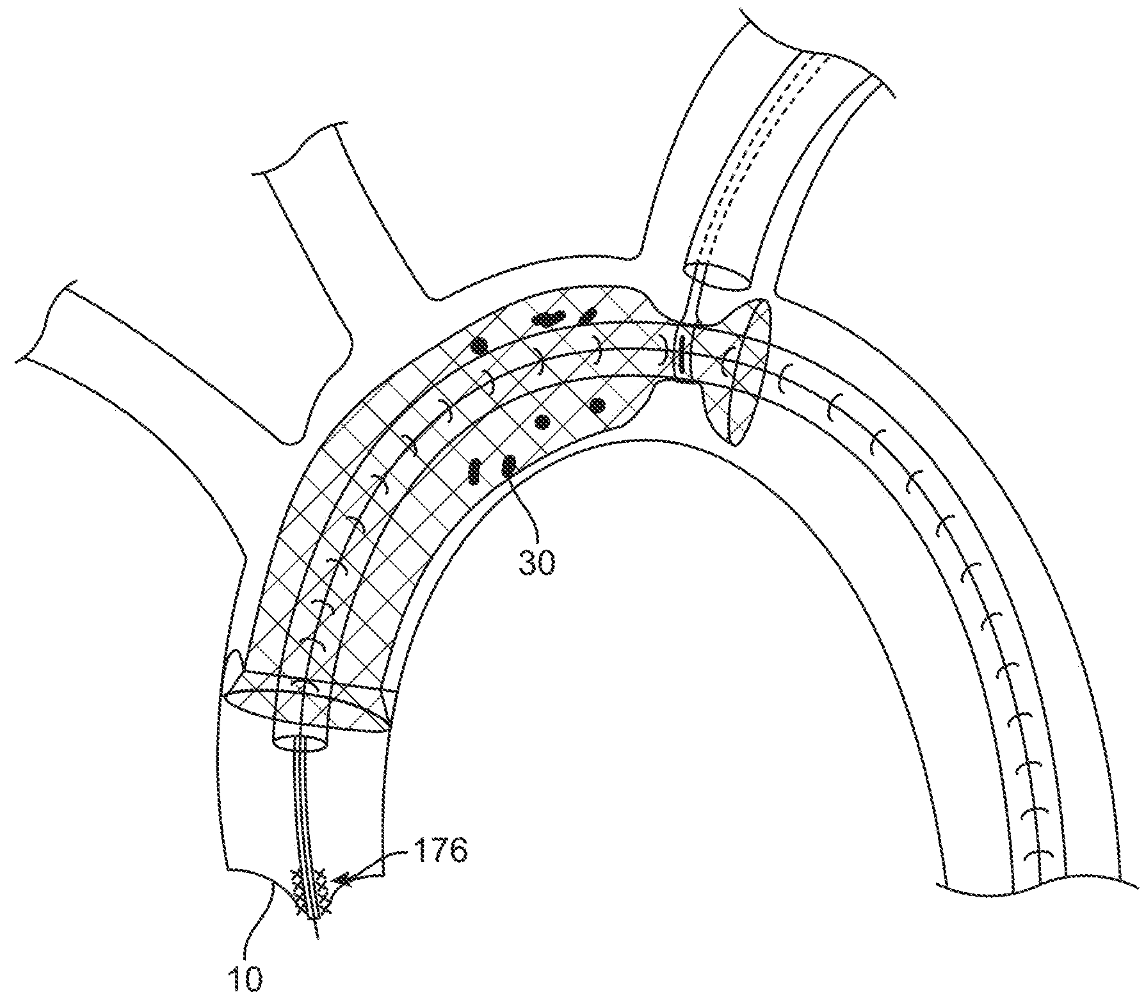
Figure 16C:
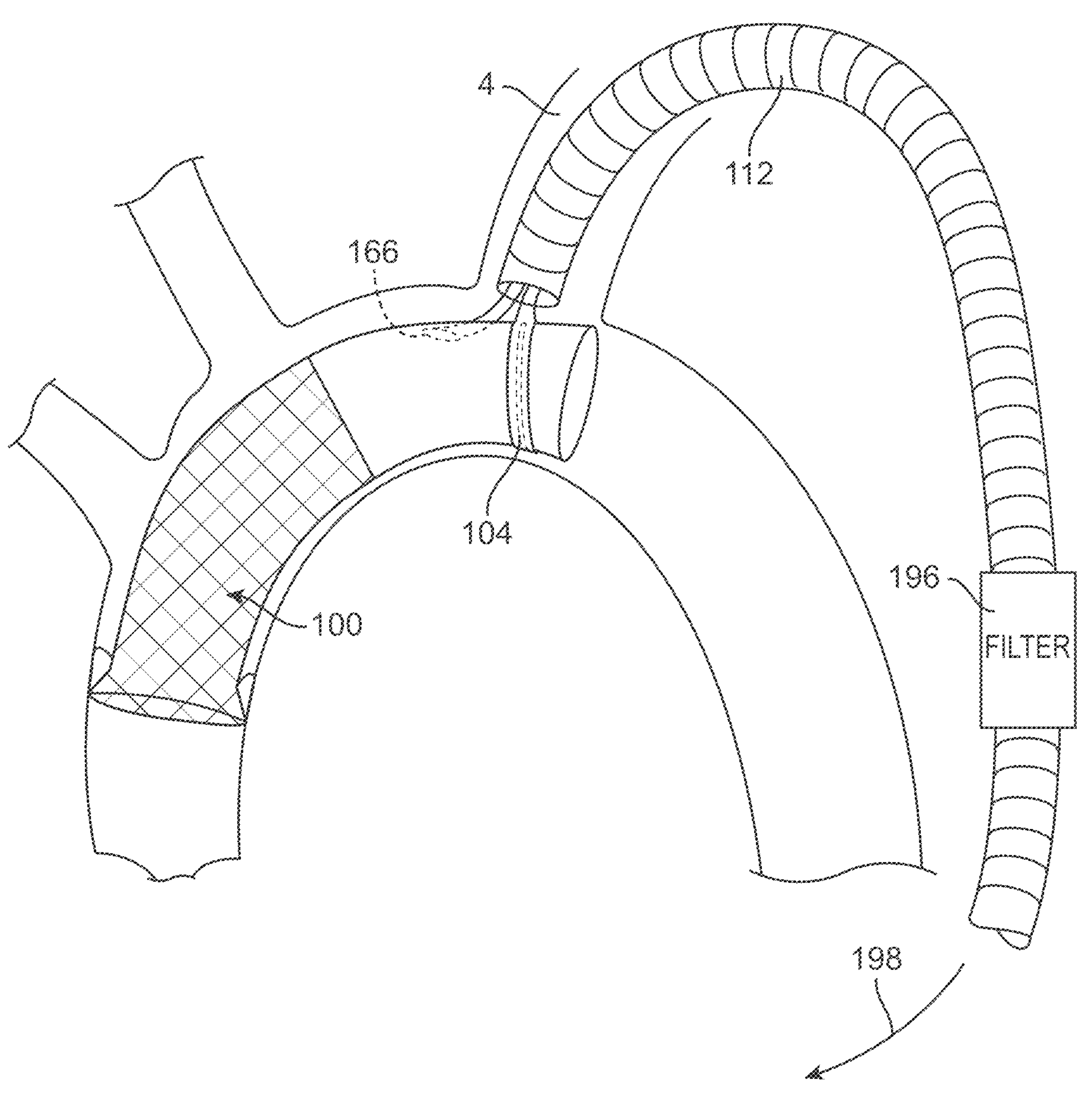

FIGS. 16A to 16C illustrate additional variations of devices for use with the procedures described herein. FIG. 16A illustrates a distal end of a TAVR guide catheter 144 with a distal end that is flared outward at multiple points 144, presumably to keep contact on the proximal edge of the balloon and possibly even to have contact on the compressed TAVR valve. The guide 130 with an inverted (or non-inverted, but simply compressed) filter could still have this flared distal end, as shown. The mesh of the filter device 100 can be folded into the guide catheter 130.

FIG. 16B shows an additional variation during or after the use with the filter devices described herein. In this example, after the filter is deployed in position (regardless of a radial or femoral approach), a custom catheter or guidewire with a "brush-like" 176 attachment advances to the procedure site to loosen any plaque or other debris from the procedure site (e.g., the valve or any other procedure site). The custom catheter 176 can be delivered to the procedure site (e.g., the aortic valve 10) prior to TAVR introduction. The brush attachment is one variation of a device that can loosen debris. For example, the brush device can have bristles or bristle-like protrusions, such as polymer fibers, arranged about the distal end. The protrusions "knock free" any loose plaque from the aortic valve prior to placing the new filter. This could be done to simply get a better fit of the new valve with respect to the aortic wall or could be done to minimize the likelihood of plaque breaking free post-procedure, especially after the filter might be removed.

Another option is to deploy the filter, as shown in FIG. 16B (either femoral or radial approach) and pre-dilate the aortic valve with a balloon catheter. The expansion of the balloon can simply allow for a better fit of the new valve with respect to the aortic wall or can be performed to minimize the likelihood of plaque breaking free post-procedure.

FIG. 16C shows a variation of returning blood through the catheter 112 extending from the left subclavian artery 4 and out of the radial artery. Once outside the patient's body, the blood can flow through a simple filter 196 with a similar pore size. Filters are readily available in paper, woven textiles, polymer, and thin-film composite materials. The constriction ring or collar 104 can still be used at the proximal region to allow the passage of the TAVR system. Alternatively, this design configuration can also be used in the patient post-procedure to collect any late-breaking emboli. In this case, the constriction ring would be completely closed, forcing all of the blood through the catheter and filter. A portion of the filter can be made impermeable to control how much blood flows into the catheter/filter loop and how much flows into the other vessels. The filtered blood can be passed back into the body via, e.g., a femoral access point 198.

Figure 17A:
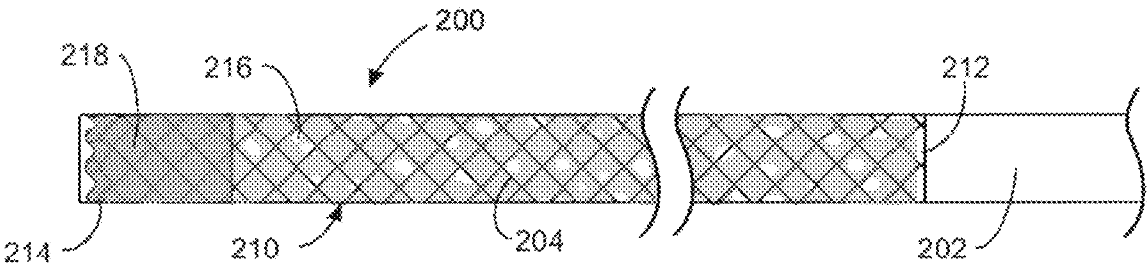
FIGS. 17A and 17B show an additional variation of a filter device that performs a sealing function.
Figure 17B:
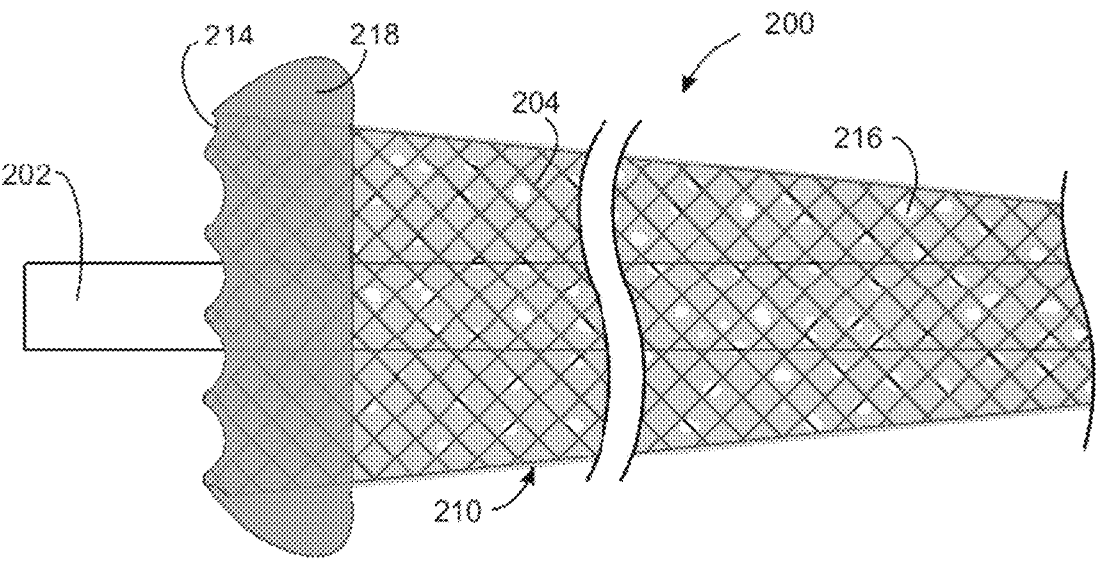

FIGS. 17A and 17B show an additional variation of a filter device 200 affixed to a medical device body 202, including but not limited to a catheter, guidewire, or other structure requiring a sealing function, as discussed herein. FIG. 17A illustrates a filter device 200 in a collapsed or delivery configuration, where the filter device 200 includes a filter body 210 having an external seal formed by an outer sail member 218 that is circumferentially located around the device 202 and a tubular member 204 that, in sated around the device 202 and a tubular member 204 that, in some variations, functions as a reinforcement structure. The filter device 200 can also include a diverting surface (not shown in FIG. 17A or 17B) positioned within the filter body 210 that redirects blood flow into the outer sail member 218. As illustrated, variations of the device 200 can include a filter body 210 that is coupled to a tubular member 204 (such as a braid, stent, or similar structure). The filter body 210 can overlay the reinforcement member 204 or can be integrated with the tubular member 204 (e.g., embedded, coated onto the tubular member 204) along an entirety or a portion of the tubular member 204. As noted below, the filter body 210 will be affixed to the tubular member 204 at proximal 210 and distal 214 ends of the filter body 210 to permit blood flow through the permeable section 216, which filters emboli from the blood. The filter device 200 can be restrained in the collapsed or delivery configuration using a restraint such as an outer sheath, wires, strings, or other structures.

FIG. 17B shows the filter device 200 in an expanded or deployed configuration where the tubular member 204 and filter body 210 expand away from the device 202 and where the outer sail 218 moves away from the filter body 210 in a radially outward direction. The outer sail can be elastic or inelastic but will deflect as a result of fluid/blood flow into an interior of the sail 218.

Figure 18A:
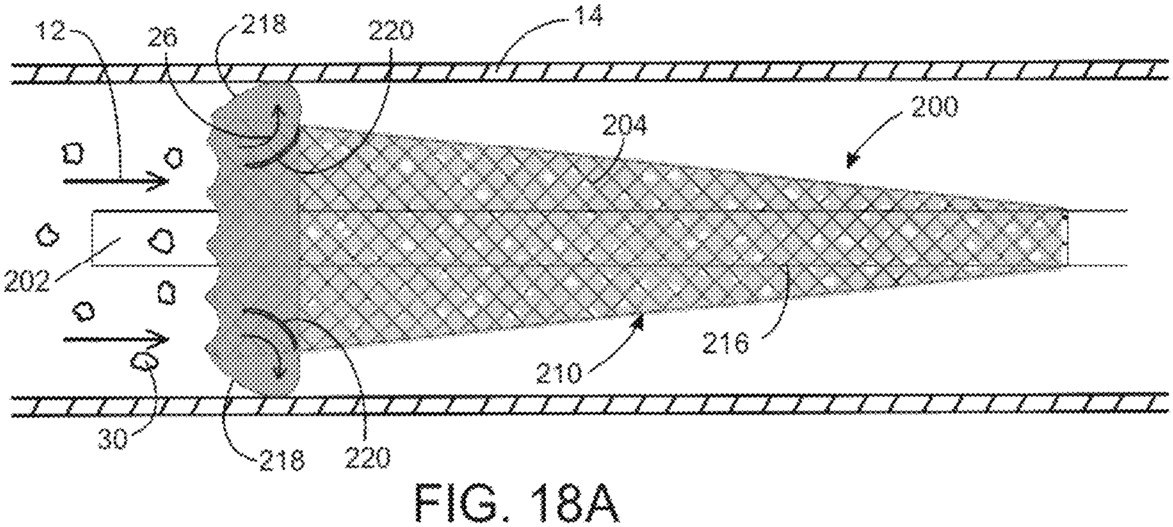
FIGS. 18A and 18B illustrate variations of the filter device shown in FIGS. 17A and 17B in a deployed configuration.
Figure 18B:
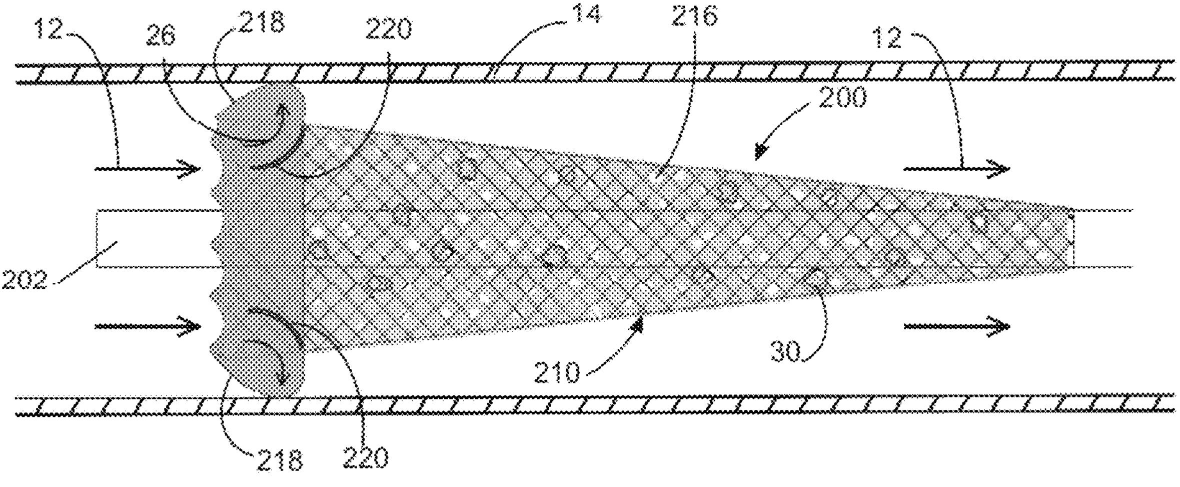
Figure 18C:
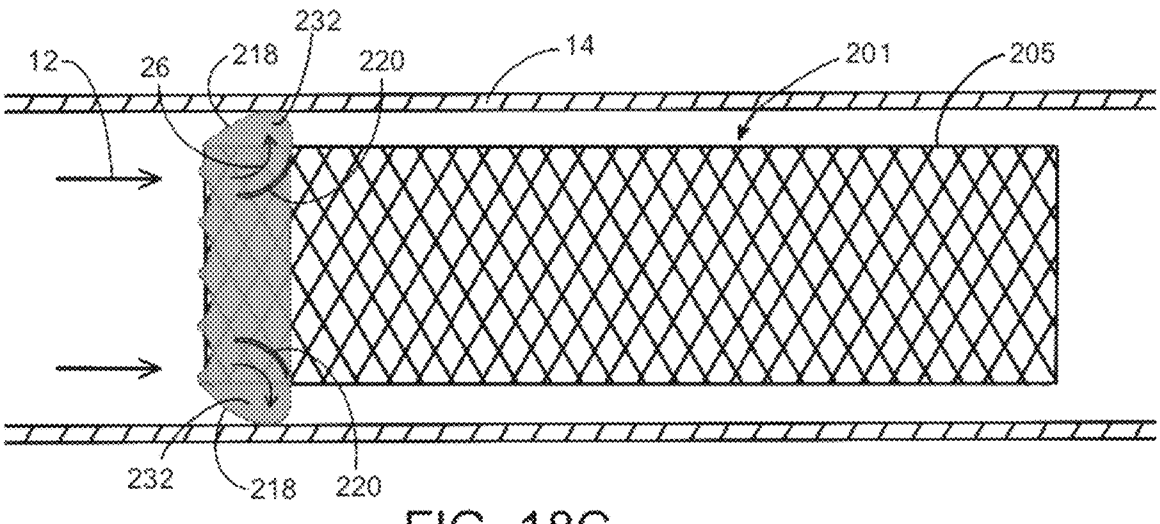
FIGS. 18C and 18D show additional variations of medical devices where the flow-directed sails are used for non-filter-type devices.
Figure 18D:
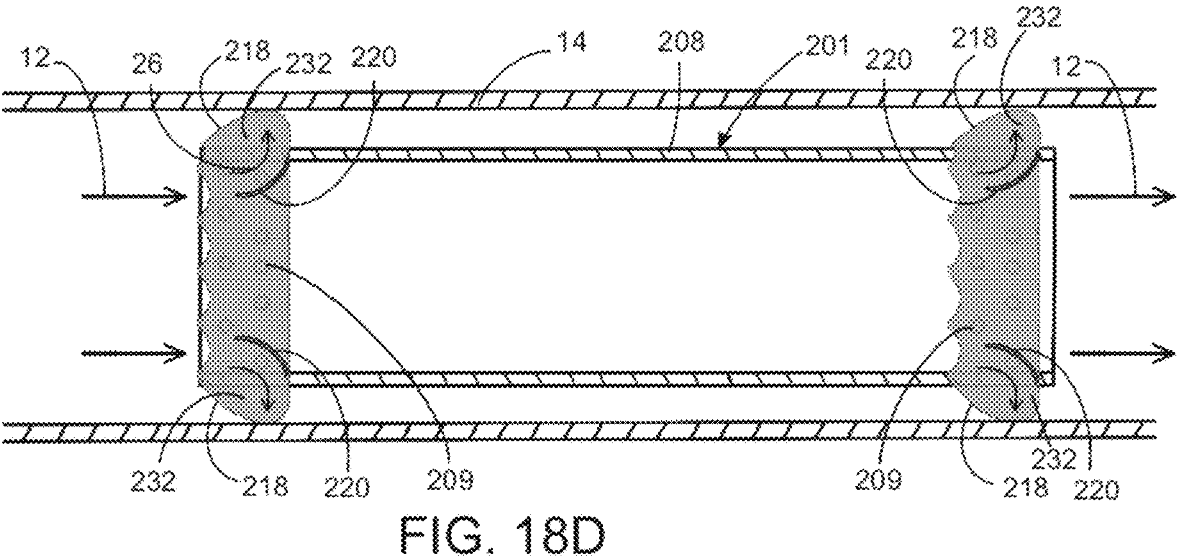

FIGS. 18A and 18B illustrate variations of the filter device 200 shown in FIGS. 17A and 17B in a deployed configuration, where blood flow 12 enters the filter body 210 and flows against an outer sail 218 that forms a seal as described herein. Blood also flows against a diverting surface 220. As discussed above with respect to FIGS. 4F and 4G, the diverting surface 220 can comprise a portion of the sealing structure (in this case, the outer sail 218), or the diverting surface 220 can comprise a separate material. In some variations, the diverting surface 220 is interior to the filter body 210. However, portions of the diverting surface 220 can extend out of or be exterior to the filter body 210. The outer sail 218 and flow-diverting surface 220 are displaced by blood flow 12 in opposite directions. The outer sail member 218 is comprised of a non-porous or low-porous material such that the flow of blood 12 moves the sail member 218 in a radially outward direction against a wall of the vessel 14 to form a seal. The diverting surface 220 shown in FIGS. 18A and 18B is shown for purposes of illustration only and can include reinforcement to prevent the diverting surface 220 from being inverted within the filter body 210. The inner sail 220 can be semi-porous or low-porous as long as it diverts some fluid flow into the outer sail 218. As shown, the diverting surface 220 redirects some blood flow 26 towards the outer sail member 218. The free end of the diverting surface 220 extends inwardly towards the device 202 while the opposing end is typically joined to the outer sail member 218 through the tubular member 204. In some variations of the device 200, the diverting surface is joined in a manner that creates a fluidly sealed joint with the outer sail 218. As shown in FIG. 18B, emboli 30 or other particulates in the blood flow 12 enter the filter body 210, which includes a fluid permeable section 216 that allows passage of blood flow out of the filter body 210 while retaining emboli 30 within.

As noted above, the construction of the outer sail member 218 has a softness or conformability that allows the flow-activated seal to expand or deform into any irregularities in the vessel to a greater degree than conventional mesh or filter device 100. This creates an improved seal between the wall 14 of the vessel and the filter device 200 to improve filtering of emboli within the bloodstream with an enhanced seal.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "an," "said," and "the" include plural references unless the context clearly dictates otherwise.

It is important to note that where possible, aspects of the various described embodiments, or the embodiments themselves can be combined. Where such combinations are intended to be within the scope of this disclosure.

I claim:

1. A medical device for forming an improved seal against a wall of a vessel using a blood flow within the vessel, the medical device comprising:

a device body configured to navigate through the vessel;

a tubular member circumferentially positioned about the device body, the tubular member having a far portion that is expandable away from the device body and a near portion coupled to the device body;

a filter body positioned exterior to the device body and coupled to the tubular member, where the filter body comprises a distal portion, a proximal portion, and a fluid permeable wall extending therebetween, where the distal portion is coupled to the far portion and the proximal portion is coupled to the device body such that when the device body is positioned in the vessel, the far portion and the distal portion expand allowing the blood flow to enter the filter body and pass through the fluid permeable wall while retaining emboli in the filter body;

an outer sail member located circumferentially about an exterior of the far portion of the tubular member, where the blood flow into the tubular member enters an interior of the outer sail member causing the outer sail member to move radially outward from the tubular member such that an exterior of the outer sail member forms a conformable seal against the wall of the vessel; and a diverting surface positioned interior to the tubular member and radially adjacent to the outer sail member, the diverting surface configured to provide resistance to the blood flow, where a second end of the diverting surface is joined to the tubular member and a first end of the diverting surface extends inwardly from the tubular member away from the outer sail member to direct the blood flow towards the outer sail member.

2. The medical device of claim 1, wherein the diverting surface is continuous with the outer sail member.

3. The medical device of claim 1, wherein the diverting surface is joined with the outer sail member.

4. The medical device of claim 1, wherein the diverting surface is non-porous or semi-porous.

5. The medical device of claim 4, wherein the first end of the diverting surface forms a conical shape.

6. The medical device of claim 1, wherein the outer sail member comprises a fluid impermeable material.

7. The medical device of claim 1, wherein the outer sail member comprises a low-porosity material.

8. The medical device of claim 1, wherein the exterior of the outer sail member comprises an elastically expandable material such that the blood flow into the interior of the outer sail member expands the outer sail member.

9. The medical device of claim 1, wherein the tubular member comprises a mesh braid.

10. The medical device of claim 9, wherein the mesh braid comprises superelastic Nitinol.

11. The medical device of claim 1, wherein the tubular member comprises a thin film polymer or elastomer.

12. The medical device of claim 1, wherein the tubular member has a pore size of 40 microns to 200 microns.

13. The medical device of claim 1, wherein the filter body comprises a sheet of material with controlled porosity.

14. The medical device of claim 1, further comprising at least one pull wire coupled to the distal portion of the filter body such that application of a tensile force on the at least one pull wire urges the distal portion to a closed position about the device body.

15. The medical device of claim 1, wherein the device body comprises a structure selected from a guidewire, a sheath, and a catheter.

16. A method for filtering a body passage for emboli dislodged during a procedure performed within the body passage of a patient, the method comprising:

positioning a filter device at a deployment site in the body passage, where the deployment site is downstream of a procedure site;

deploying the filter device such that a blood flow towards the filter device causes an external sail located about an outer perimeter of the filter device to move away from the filter device and form a seal against a wall of the body passage, where a diverting surface located within the filter device redirects a portion of the blood flow towards an interior of the external sail, and where a body of the filter device permits passage of the blood flow while restricting flow of emboli such that emboli within the blood flow is retained within the filter device;

securing the filter device and emboli located therein after the procedure; and removing the filter device and emboli from the body passage.

17. A medical device for forming an improved seal against a vessel wall of a vessel using a fluid flow within the vessel, the medical device comprising:

a tubular member having a far portion, a near portion, and a wall extending therebetween;

an outer sail member located circumferentially about an exterior of the far portion of the tubular member, where the fluid flow into the tubular member enters an interior of the outer sail member causing the outer sail member to move radially outward from the tubular member such that an exterior of the outer sail member forms a conformable seal against the vessel wall; and a diverting surface located interior to the tubular member and radially adjacent to the outer sail member, the diverting surface having a first end, a second end, and an intermediate portion extending therebetween, where the first end extends inwardly away from the outer sail member causing the intermediate portion to direct the fluid flow towards the outer sail member.

18. The medical device of claim 17, wherein the tubular member comprises a structure selected from a group comprising a stent graft, a stent, a shunt, and a flow diverter.

19. The medical device of claim 17, wherein the tubular member comprises a guidewire.

20. The medical device of claim 17, wherein the tubular member comprises a catheter body configured to navigate through the vessel.

* * * * *